US009085611B2

(12) United States Patent
Yamano et al.

(10) Patent No.: US 9,085,611 B2
(45) Date of Patent: *Jul. 21, 2015

(54) HUMANIZED PCRV ANTIBODY HAVING ANTI-PSEUDOMONAL ACTIVITY

(71) Applicant: Shionogi & Co., Ltd., Osaka-shi, Osaka (JP)

(72) Inventors: Yoshinori Yamano, Osaka (JP); Yoshito Numata, Osaka (JP); Takafumi Sato, Toyonaka (JP); Toshinaga Tsuji, Osaka (JP); Keiko Kawamoto, Osaka (JP)

(73) Assignee: SHIONOGI & CO., LTD., Osaka-Shi (JP)

( * ) Notice: Subject to any disclaimer, the term of this patent is extended or adjusted under 35 U.S.C. 154(b) by 72 days.

This patent is subject to a terminal disclaimer.

(21) Appl. No.: 13/734,872

(22) Filed: Jan. 4, 2013

(65) Prior Publication Data
US 2013/0108627 A1 May 2, 2013

Related U.S. Application Data

(62) Division of application No. 13/256,219, filed as application No. PCT/JP2010/053828 on Mar. 9, 2010.

(30) Foreign Application Priority Data

Mar. 11, 2009 (JP) ................. 2009-057929

(51) Int. Cl.
*C07K 16/00* (2006.01)
*C07K 16/12* (2006.01)

(52) U.S. Cl.
CPC ......... *C07K 16/1214* (2013.01); *C07K 2317/24* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,551,795 | B1 | 4/2003 | Rubenfield et al. |
| 2004/0208888 | A1 | 10/2004 | Frank et al. |
| 2005/0063985 | A1 | 3/2005 | Frank et al. |
| 2009/0117121 | A1 | 5/2009 | Tanaka et al. |
| 2011/0150896 | A1 | 6/2011 | Numata et al. |

FOREIGN PATENT DOCUMENTS

| | | |
|---|---|---|
| EP | 2011867 A1 | 1/2009 |
| EP | 2175017 A1 | 4/2010 |
| JP | 2005-500250 A | 1/2005 |
| JP | 2007/533304 A | 11/2007 |
| WO | WO-02/064161 A2 | 8/2002 |
| WO | WO-2004/099250 A1 | 11/2004 |
| WO | WO-2005/066970 A2 | 7/2005 |
| WO | WO-2007/114340 A1 | 10/2007 |
| WO | WO-2009005040 A1 | 1/2009 |
| WO | WO-2009-073631 A2 | 6/2009 |
| WO | WO-2009/088032 A1 | 7/2009 |
| WO | WO-2010/104052 A1 | 9/2010 |

OTHER PUBLICATIONS

Spack, E.G. et al., "Humanized Anti-Perv Monoclonal Antibody IM166 Binds to the Type III Toxin Delivery System of *Pseudomonas aeruginosa* and Prevents Mortality in an Animal Model of *Pseudomonas*-Induced Pneumonia", FASEB Journal, vol. 16, No. 4, 2002.—XP008007107.

Baer, M. et al., "An engineered human antibody fab fragment specific for *Pseudomonas aeruginosa* PcrV antigen has antibacterial activity", Infection and Immunity, vol. 77, No. 3, pp. 1083-1090, 2009.—XP002581947.

European Search Report—EP09701235.5—PCT/JP2009050118, Feb. 2009.

Yahr, T. L., et al., "Identification of Type III Secreted Products of *Pseudomonas aeruginosa* Exoenzyme S Regulon." J. of Bacter., vol. 179, No. 22, pp. 7165-7168 (1997).

Sawa, T., et al., "Active and passive immunization with the *Pseudomonas* V antigen protects against type III intoxication and lung injury," Nat. Med., vol. 5, No. 4, pp. 392-398 (1999).

Shime, N., et al, "Therapeutic Adminstration Anti-PcrV F(ab')2 in Sepsis Associated with *Pseudomonas aeruginosa*," J. Immunol., vol. 167, pp. 5880-5886 (2001).

Imamura, Y., et al., "Effect of anti-PcrV antibody in a murine chronic airway *Pseudomonas aeruginosa* infection model," Eur. Respir. J., vol. 29, No. 5, pp. 965-968 (2007).

Faure, K., et al., "Effect of monoclonal anti-PcrV antibody of *Pseudomonas aeruginosa*-induced acute lung injury in a rat model," J. Immune Based Therapies & Vaccines, vol. 1 (2003).

Frank, D. W., et al., "Generation and Characterization of a Protective Monoclonal Antibody to *Pseudomonas aeruginosa* PcrV," J. Infect. Dis., vol. 186, pp. 64-73 (2002).

Neely, A.N. et al., "Passive anti-PcrV treatment protects burned mice against Pseudomonas aeruginosa challenge", Burns, vol. 31, No. 2, pp. 153-158, 2005.—XP004729362.

Kipnis, E. et al., "Targeting mechanisms of Pseudomonas aeruginosa pathogenesis", Medecine et Maladies Infectieuses, vol. 36, No. 2, pp. 78-91, 2006.—XP025087331.

(Continued)

*Primary Examiner* — Laura B Goddard
*Assistant Examiner* — Meera Natarajan
(74) *Attorney, Agent, or Firm* — Birch, Stewart, Kolasch & Birch, LLP

(57) ABSTRACT

Provided are a humanized monoclonal antibody against PcrV or a part thereof, and a pharmaceutical composition containing the same as an active ingredient, as an effective means for therapy of infection, particularly infection with *Pseudomonas aeruginosa*. Concretely, the humanized monoclonal antibody of the present invention has an excellent inhibitory activity on the cytotoxicity with respect to a target cell of *Pseudomonas aeruginosa*. Also, the humanized monoclonal antibody of the present invention has a high affinity for PcrV.

4 Claims, 10 Drawing Sheets

(56) References Cited

OTHER PUBLICATIONS

Spack, E.G. et al., "Humanized Anti-Pcn/ Monoclonal Antibody IM166 Binds to the Type III Toxin Delivery System of Pseudomonas Aeruginosa and Prevents Mortality in an Animal Model of Pseudomonas-Induced Pneumonia", FASEB Journal, vol. 16, No. 4, 2002.—XP008007107.

Moss, J. et al., "Sera from adult patients with cystic fibrosis contain antibodies to Pseudomonas aeruginosa type III apparatus", Infection and Immunity, vol. 69, No. 2, pp. 1185-1188, 2001.—XP002615882.

Baer, M. et al., "An engineered human antibody fab fragment specific for Pseudomonas aeruginosa PcrV antigen has potent antibacterial activity", Infection and Immunity, vol. 77, No. 3, pp. 1083-1090, 2009.—XP002581947.

European Search Report—EP09701235.5—PCT/JP2009050118.

Yahr, T. L., et al., "Identification of Type III Secreted Products of *Pseudomonas aeruginosa* Exoenzyme S Regulon," J. Of Bacter., vol. 179, No. 22, pp. 7165-7168 (1997).

Sawa, T., et al., "Active and passive immunization with the *Pseudomonas V* antigen protects against type III intoxication and lung injury," Nat. Med., vol. 5, No. 4, pp. 392-398 (1999).

Shime, N., et al, "Therapeutic Administration of Anti-PcrV F(ab')2 in Sepsis Associated with *Pseudomonas aeruginosa*," J. Immunol., vol. 167, pp. 5880-5886 (2001).

Imamura, Y., et al., "Effect of anti-PcrV antibody in a murine chronic airway *Pseudomonas aeruginosa* infection model," Eur. Respir. J., vol. 29, No. 5, pp. 965-968 (2007).

Faure, K., et al., "Effects of monoclonal anti-PcrV antibody on *Pseudomonas aeruginosa*-induced acute lung injury in a rat model," J. Immune Based Therapies & Vaccines, vol. 1, (2003).

Frank, D. W., et al., "Generation and Characterization of a Protective Monoclonal Antibody to *Pseudomonas aeruginosa* PcrV," J. Infect. Dis., vol. 186, pp. 64-73 (2002).

NCBI Sequence Revision History [online] AccessionAF010149, Retrieval date Feb. 13, 2009.

Figure 1
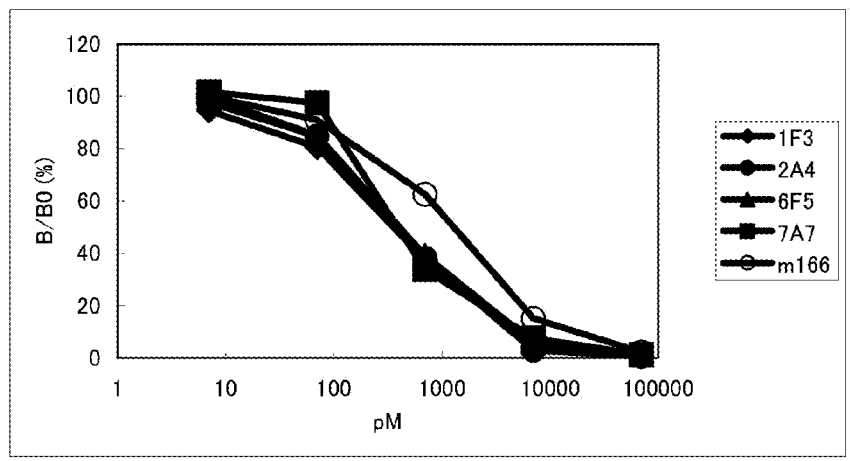
Figure 2
| Clone | Kd (M) |
|---|---|
| m166 | $3.0 \times 10^{-9}$ |
| 1F3 | $3.7 \times 10^{-10}$ |
| 2A4 | $3.5 \times 10^{-10}$ |
| 6F5 | $1.1 \times 10^{-10}$ |
| 7A7 | $1.1 \times 10^{-9}$ |
Figure 3
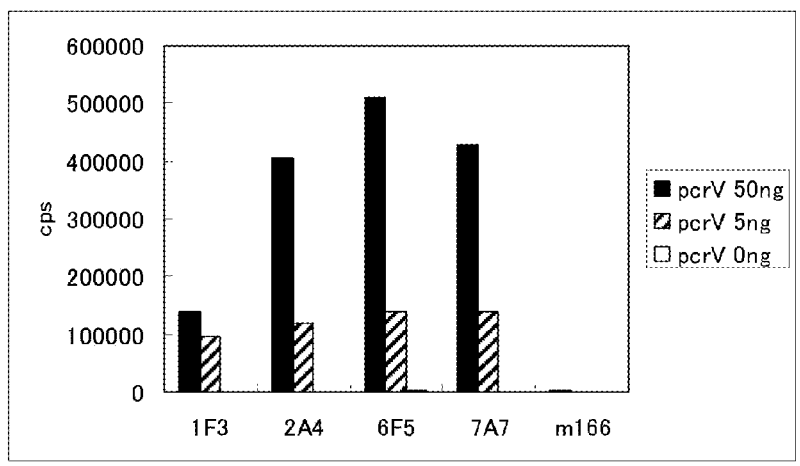

Figure 8
Suppression of neutralizing activity with full-length PcrV

Figure 9

Suppression of neutralizing activity with truncated PcrV

Figure 10

(SEQ ID NO: 11, 12)

Heavy Chain

QVQLQQPGAELVKPGASVKLSCKASGY<u>SFTSYWMH</u>WVKQRPGQGLEWIG<u>EINPSN
GRTNYNEKFNT</u>KATLTVDTSSSTAYMQLSSLTSEDSAVYYCVL<u>YGNYVVYYTMDY</u>W
GQGTSVTVSS

Light Chain

QIVLTQSPTIMSASLGEEITLTC<u>SASTSVSYME</u>WYQQKSGTSPKILIY<u>TTSKLAS</u>GVPS
RFSGSGSGTFYSLTISSVEAEDAADYYC<u>HQWRNYPFT</u>FGSGTKLEIKRAD

Figure 11
(SEQ ID NO: 13, 14)

Heavy Chain

DVQLQESGPGLVKPSQSLSLTCTVTGY<u>SITSDYAWN</u>WIRQFPGNKLEWMG<u>YITYNG
DTSYNPSLKS</u>RISIARDTSKNQFFLQLNSVTTEDTATYSCAG<u>SRNYYGAWFAY</u>WGQG
TLVTVSA

Light Chain

DIVMTQSHKFMSTSIGDRVSINY<u>KASQYVGTTVA</u>WYQQKSGHSPKLLIY<u>RASTRHT</u>G
VPDRFTGSGSGTDFTLNISNVQSEDLADYFC<u>QQYCSSPLT</u>FGAGTYLEVKRAD

Figure 12

Heavy chain

```
                                              CDRH1                 CDRH2
Mouse 1F3      1:QVQLQQPGAELVKPGASVKLSCKASGYSFTSYWMHWVKQRPGQGLEWIGEINPSNGRTNY 60
Template       1:QVQLVQSGAEVKKPGASVKVSCKASGYSFTSYWMHWVRQAPGQGLEWMGEINPSNGRTNY 60
Backmutation   1:QVQLVQSGAEVKKPGASVKVSCKASGYSFTSYWMHWVRQAPGQGLEWMGEINPSNGRTNY 60
Humanized 1F3  1:QVQLVQSGAEVKKPGASVKVSCKASGYSFTSYWMHWVRQAPGQGLEWMGEINPSNGRTNY 60
                 ****.*.***..*******.*****************.*.*******.************
                                                  CDRH3
Mouse 1F3     61:NEKFNTKATLTVDTSSSTAYMQLSSLTSEDSAVYYCVLYGNYVVYYTMDYWGQGTSVTVS 120
Template      61:NEKFNTRVTMTRDTSTSTVYMELSSLRSEDTAVYYCARYGNYVVYYTMDYWGQGTTVTVS 120
Backmutation  61:NEKFNTRVTMTRDTSTSTVYMELSSLRSEDTAVYYCVLYGNYVVYYTMDYWGQGTTVTVS 120
Humanized 1F3 61:NEKFNTRVTMTRDTSTSTVYMELSSLRSEDTAVYYCVLYGNYVVYYTMDYWGQGTTVTVS 120
                 ******..*.*.***.**.**.****.***.*****..*****************.****

Mouse 1F3    121:S                                                             121
Template     121:S                                                             121
Backmutation 121:S                                                             121
Humanized 1F3 121:S                                                            121
                 *
```

Light chain

```
                                              CDRL1                 CDRL2
Mouse 1F3      1:QIVLTQSPTIMSASLGEEITLTCSASTSVSYMEWYQQKSGTSPKILIYTTSKLASGVPSR 60
Template       1:DIQLTQSPSFLSASVGDRVTITCSASTSVSYMEWYQQKPGKAPKLLIYTTSKLASGVPSR 60
Backmutation   1:DIQLTQSPSFLSASVGDRVTITCSASTSVSYMEWYQQKPGKAPKLLIYTTSKLASGVPSR 60
Humanized 1F3  1:DIQLTQSPSFLSASVGDRVTITCSASTSVSYMEWYQQKPGKAPKLLIYTTSKLASGVPSR 60
                 .*.*****...***.*...*.*****************.*...**.**************
                                   CDRL3
Mouse 1F3     61:FSGSGSGTFYSLTISSVEAEDAADYYCHQWRNYPFTFGSGTKLEIKRA          108
Template      61:FSGSGSGTEFTLTISSLQPEDFATYYCHQWRNYPFTFGQGTKLEIKRA          108
Backmutation  61:FSGSGSGTEFTLTISSLQPEDFATYYCHQWRNYPFTFGQGTKLEIKRA          108
Humanized 1F3 61:FSGSGSGTEFTLTISSLQPEDFATYYCHQWRNYPFTFGQGTKLEIKRA          108
                 ********...*****...**.*.***********.*********
```

Figure 13

| Heavy Chain | Light Chain | ka(1/Ms) | kd(1/s) | KD(M) |
|---|---|---|---|---|
| H chimera | L chimera | $2.0 \times 10^6$ | $5.1 \times 10^{-4}$ | $2.6 \times 10^{-10}$ |
| HT | LT | $1.1 \times 10^5$ | $2.5 \times 10^{-2}$ | $2.2 \times 10^{-7}$ |
| HT | LB | $6.2 \times 10^4$ | $4.0 \times 10^{-2}$ | $6.5 \times 10^{-7}$ |
| HB | LT | $1.4 \times 10^6$ | $4.8 \times 10^{-4}$ | $3.3 \times 10^{-10}$ |
| HB | LB | $1.3 \times 10^6$ | $4.2 \times 10^{-4}$ | $3.4 \times 10^{-10}$ |

Figure 14

| Heavy Chain | Light Chain | ka(1/Ms) | kd(1/s) | KD(M) |
|---|---|---|---|---|
| H chimera | L chimera | $8.5 \times 10^5$ | $2.3 \times 10^{-4}$ | $2.7 \times 10^{-10}$ |
| HB | LT | $5.4 \times 10^5$ | $1.8 \times 10^{-4}$ | $3.4 \times 10^{-10}$ |
| I48M | LT | $8.5 \times 10^5$ | $1.2 \times 10^{-4}$ | $1.5 \times 10^{-10}$ |
| A67V | LT | $7.5 \times 10^5$ | $1.6 \times 10^{-4}$ | $2.1 \times 10^{-10}$ |
| L69M | LT | $6.8 \times 10^5$ | $1.7 \times 10^{-4}$ | $2.5 \times 10^{-10}$ |
| V71R | LT | $7.2 \times 10^5$ | $1.6 \times 10^{-4}$ | $2.2 \times 10^{-10}$ |
| A78V | LT | $1.9 \times 10^6$ | $4.6 \times 10^{-5}$ | $2.4 \times 10^{-11}$ |
| V93A | LT | $2.0 \times 10^6$ | $5.1 \times 10^{-4}$ | $2.6 \times 10^{-10}$ |
| L94R | LT | $6.2 \times 10^4$ | $4.0 \times 10^{-2}$ | $6.5 \times 10^{-7}$ |

Figure 15
SEQ ID NO: 27

QVQLVQSGAEVKKPGASVKVSCKASGY<u>SFTSYWMH</u>WVRQAPGQGLEWMG<u>EINPSNGRTNY
NEKFN</u>TRVTMTRDTSTSTVYMELSSLRSEDTAVYYCVL<u>YGNYVVYYTMDY</u>WGQGT

Figure 16
SEQ ID NO: 28

DIQLTQSPSFLSASVGDRVTITC<u>SASTSVSYME</u>WYQQKPGKAPKLLIY<u>TTSKLAS</u>GVPSRFSGS
GSGTEFTLTISSLQPEDFATYYC<u>HQWRNYPFT</u>FGQGTKLEIK

Figure 17

| Heavy Chain | Light Chain | ka(1/Ms) | kd(1/s) | KD(M) |
|---|---|---|---|---|
| H chimera | L chimera | $7.4 \times 10^5$ | $3.7 \times 10^{-4}$ | $4.9 \times 10^{-10}$ |
| h1F3 H | h1F3 L | $8.7 \times 10^5$ | $3.3 \times 10^{-4}$ | $3.8 \times 10^{-10}$ |

HUMANIZED PCRV ANTIBODY HAVING ANTI-PSEUDOMONAL ACTIVITY

This application is a Continuation Application which claims priority under 35 U.S.C. §120 of U.S. application Ser. No. 13/256,219 filed on Sep. 12, 2011, which is the National Phase under 35 U.S.C. §371 of International Application No. PCT/JP2010/053828 filed on Mar. 9, 2010, which claims priority under 35 U.S.C. §119(a)-(d) of Application No. 2009-057929 filed in Japan on Mar. 11, 2009. All of these applications are hereby incorporated by reference for all purposes.

TECHNICAL FIELD

The present invention relates to a humanized monoclonal antibody that recognizes PcrV, or a part thereof. More specifically, the present invention relates to an antibody having higher neutralizing activity (hereinafter, also referred to as cytotoxicity inhibiting activity) than conventional anti-PcrV antibodies, or a part thereof, and a pharmaceutical composition containing the same.

BACKGROUND ART

*Pseudomonas aeruginosa* is obligately aerobic gram negative *bacillus* being widely existing in the natural world. Although its pathogenicity is usually low, it is a pathogen that causes opportunistic infections often occurring in patients suffering from various pre-existing diseases such as cancer and diabetes, and in patients administered with pharmaceuticals having immune-inhibitory action, and may often cause pneumonia, urinary tract infection, sepsis or the like to lead to severe results. In clinical fields, *pseudomonas aeruginosa* infection is considered as one of the most difficult infections to be treated because *Pseudomonas aeruginosa* not only has inherently low sensitivity to existent antibiotics, but also has high tendency to easily acquire resistance to various antibiotics and to become difficult to cure. Thus for *Pseudomonas aeruginosa*, the measure of developing new antibiotics one after another is limited, and a therapeutic method that does not rely on antibiotics is strongly desired.

High cytotoxicity of *Pseudomonas aeruginosa* is exerted by injection of toxin into a eukaryotic cell via a type III exotoxin secretion system. PcrV is a protein of 294 residues (NCBI Accession No. AAC45935, SEQ ID NO: 1) constituting the type III exotoxin secretion system, and an operon sequence encoding the same is open to the public (Patent document 1, Non-patent document 1). Since control for PcrV can possibly lead a therapeutic means in *pseudomonas aeruginosa* infection (Non-patent document 2), polyclonal antibodies (Non-patent documents 3, 4) and monoclonal antibodies (Patent document 2, Non-patent documents 5, 6) against PcrV having neutralizing activity are reported. However, polyclonal antibodies are difficult to be humanized and to be used as pharmaceutical compositions because of difficulty in improvement of antigenicity. Also the monoclonal antibodies having reported heretofore have low neutralizing activity and fail to satisfy requirements in clinical fields.

Patent document 1: U.S. Pat. No. 6,551,795
Patent document 2: Japanese Translation of PCT publication No. 2005-500250
Non-patent document 1: Yahr, T. L. et al., J. Bacteriol., 1997, vol. 179, p. 7165
Non-patent document 2: T. Sawa et al., Nature Medicine, 1999, vol. 5, p. 392
Non-patent document 3: Shime N et al., J. Immunol. 2001, vol. 167, p. 5880
Non-patent document 4: Imamura Y et al., Eur. Respir. J., 2007, Vol. 29, p. 965
Non-patent document 5: Karine Faure et al., J. Immune. Based. Therapies and Vaccines, 2003, Vol. 1
Non-patent document 6: Dara W. Frank et al., J. Infect. Disease, 2002, Vol. 186, p. 64

SUMMARY OF THE INVENTION

Problem to be Solved by the Invention

It is an object of the present invention to provide a measure that is effective in therapy of infection, in particular, infection with *pseudomonas aeruginosa*.

Means for Solving the Problem

As a result of diligent efforts on preparation of monoclonal antibody against PcrV, the present inventors have succeeded in preparing a novel humanized monoclonal antibody which is considered to have higher therapeutic effect on disease, compared to a conventionally known anti-PcrV monoclonal antibody, and have completed the present invention.

To be more specific, the present invention relates to:
(1) a humanized monoclonal antibody against PcrV or a part thereof, having at least one feature selected from (A) to (D):
  (A) inhibiting 50% or more of cytotoxicity to leukocyte cell of *Pseudomonas aeruginosa* at a concentration of 1 nM to 200 nM in vitro;
  (B) inhibiting 50% or more of cytotoxicity to myeloma cell of *Pseudomonas aeruginosa* at a concentration of 1 nM to 50 nM in vitro;
  (C) having a dissociation constant (Kd) with PcrV of $2\times10^{-9}$ (M) or less; and
  (D) having its epitope at positions of 136 to 233 in amino acid sequence of SEQ ID NO: 1;
(2) a humanized monoclonal antibody or a part thereof, having amino acid sequence where complementarity determining region (CDR) of monoclonal antibody produced by hybridoma deposited as an accession number of FERM ABP-11805;
(3) a humanized monoclonal antibody against PcrV or a part thereof, having
1) in a complementarity determining region, a heavy chain variable region including the following amino acid sequence: SFTSYWMH (SEQ ID NO: 15), INPSNGRTNYNEKFNT (SEQ ID NO: 16), YGNYVVYYTMDY (SEQ ID NO: 17) and 2) in a complementarity determining region, a light chain variable region including the following amino acid sequence: SASTSVSYME (SEQ ID NO: 18), TTSKLAS (SEQ ID NO: 19), HQWRNYPFT (SEQ ID NO: 20);
(4) a humanized monoclonal antibody against PcrV or a part thereof, having
1) in a complementarity determining region, a heavy chain variable region including the following amino acid sequence: SFTSYWMH (SEQ ID NO: 15), INPSNGRTNYNEKFNT (SEQ ID NO: 16), YGNYVVYYTMDY (SEQ ID NO: 17) or in at least one CDR of the three CDR set, a heavy chain variable region including those having substitution, addition or deletion of one or several amino acid and
2) in a complementarity determining region, a light chain variable region including the following amino acid sequence: SASTSVSYME (SEQ ID NO: 18), TTSKLAS (SEQ ID NO: 19), HQWRNYPFT (SEQ ID NO: 20) or in at least one CDR of the three CDR set, a light chain variable region including those having substitution, addition or deletion of one or several amino acid, and at least one feature selected from (A) to (D):

(A) inhibiting 50% or more of cytotoxicity to leukocyte cell of *Pseudomonas aeruginosa* at a concentration of 1 nM to 200 nM in vitro;

(B) inhibiting 50% or more of cytotoxicity to myeloma cell of *Pseudomonas aeruginosa* at a concentration of 1 nM to 50 nM in vitro;

(C) having a dissociation constant (Kd) with PcrV of $2 \times 10^{-9}$ (M) or less; and (D) having its epitope at positions of 136 to 233 in amino acid sequence of SEQ ID NO: 1;

(5) a humanized monoclonal antibody against PcrV or a part thereof, having 1) a heavy chain variable region having amino acid sequence of SEQ ID NO: 27, and 2) a light chain variable region having amino acid sequence of SEQ ID NO: 28;

(6) a pharmaceutical composition comprising the antibody or a part thereof according to any one of (1) to (5), as an active ingredient;

(7) a polynucleotide encoding a heavy chain variable region and a light chain variable region of antibody according to any one of (3) to (5);

(8) an expression vector comprising of the polynucleotide according to (7);

(9) a method for the treatment of infectious diseases induced by *Pseudomonas aeruginosa*, comprising: administering an effective amount of the monoclonal antibody or part thereof according to any one of (1) to (5);

(10) use of the monoclonal antibody or part thereof according to any one of (1) to (5) in the preparation of a medicament for treating infectious diseases induced by *Pseudomonas aeruginosa*; and

(11) a pharmaceutical composition comprising the antibody or a part thereof according to any one of (1) to (5) for treating infectious diseases induced by *Pseudomonas aeruginosa*.

Effect of the Invention

A humanized monoclonal antibody or a part thereof of the present invention is useful as a prevention agent and/or a treatment agent of infectious diseases induced by *Pseudomonas aeruginosa* because of its very excellent neutralizing activity on PcrV.

BRIEF EXPLANATION OF DRAWINGS

FIG. 1 shows curves in which biotin-labeled PcrV is substituted by non-labeled PcrV in PcrV antibodies (1F3, 2A4, 6F5, 7A7 and Mab166).

FIG. 2 shows affinities of PcrV antibodies (1F3, 2A4, 6F5, 7A7 and Mab166) determined by surface plasmon resonance analysis.

FIG. 3 shows results of sandwich assays between PcrV antibodies (1F3, 2A4, 6F5, 7A7 and Mab166) and Mab166.

FIG. 8 shows correlation between antibody and full-length PcrV by suppression of cytotoxicity inhibiting activity.

FIG. 9 shows correlation between antibody and truncated PcrV by suppression of cytotoxicity inhibiting activity.

FIG. 10 shows amino acid sequence of a variable region of 1F3 antibody. The underline indicates a CDR region.

FIG. 11 shows amino acid sequence of a variable region of 2A4 antibody. The underline indicates a CDR region.

FIG. 12 shows an alignment of the amino acid sequences of the heavy and light chain variable regions of the mouse antibody (Mouse 1F3), the template humanized antibody (Template), the mutant humanized antibody (Backmutation) and the humanized antibody (Humanized 1F3).

FIG. 13 shows the affinity between the PcrV antigen and each combination of the heavy chain of a mouse-human chimeric antibody (H chimera), the light chain thereof (L chimera), the heavy chain of the template humanized antibody (HT), the light chain thereof (LT), the heavy chain of the mutant humanized antibody (HB), and the light chain thereof (LB).

FIG. 14 shows the affinity of the antibodies including each of the combinations of the mouse-human chimeric antibody heavy chain (H chimera), the mouse-human chimeric antibody light chain (L chimera), the mutant humanized antibody heavy chain mutants (148M, A67V, L69M, V71R, A78V, V93A and L94R), and the template humanized antibody light chain (LT), with the PcrV antigen.

FIG. 15 shows amino acid sequence of a heavy chain variable region of humanized antibody. The underline indicates a CDR region.

FIG. 16 shows amino acid sequence of a light chain variable region of humanized antibody. The underline indicates a CDR region.

FIG. 17 shows the affinity between the PcrV antigen and each combination of the heavy chain of a mouse-human chimeric antibody (H chimera), the light chain thereof (L chimera), the heavy chain of the humanized antibody (h1F3 H), and the light chain thereof (h1F3 L).

MODE FOR CARRYING OUT THE INVENTION

Figure 4:
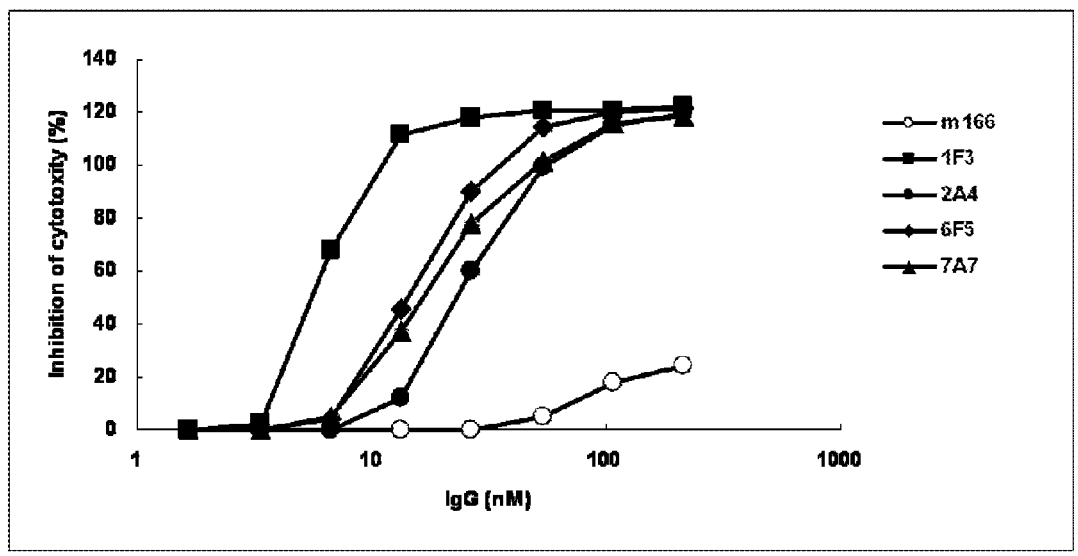
FIG. 4 shows inhibiting effects of PcrV antibodies (1F3, 2A4, 6F5, 7A7 and Mab166) on cytotoxicity to U937 cells of *Pseudomonas aeruginosa* strain SR24.

"Monoclonal antibody" which is an object of the present invention is a monoclonal antibody that specifically binds to the above-mentioned PcrV. More concretely, it is a monoclonal antibody against PcrV having at least one feature selected from (1) inhibiting 50% or more of cytotoxicity to leukocyte cell by *Pseudomonas aeruginosa* at a concentration of 1 nM to 200 nM in vitro; (2) inhibiting 50% or more cytotoxicity to myeloma cell by *Pseudomonas aeruginosa* at a concentration of 1 nM to 50 nM in vitro; (3) having a dissociation constant (Kd) with PcrV of $2 \times 10^{-9}$ (M) or less; and (4) having its epitope at positions of 136 to 233 in amino acid sequence of SEQ ID NO: 1.

One feature of the monoclonal antibody of the present invention is to have strong cytotoxicity inhibiting activity. For example, when leukocyte cell is used, the monoclonal antibody has such inhibiting (neutralizing) activity that inhibits 50% or more cytotoxicity of *Pseudomonas aeruginosa*, at a concentration range from 1 to 200 nM, preferably from 2 to 100 nM, and more preferably from 5 to 25 nM. When myeloma cell is used, the monoclonal antibody has such inhibiting (neutralizing) activity that inhibits 50% or more cytotoxicity of *Pseudomonas aeruginosa*, at a concentration range from 1 to 50 nM, preferably from 2 to 30 nM, and more preferably from 4 to 20 nM. These values largely exceed the numerical activities for Mb166 reported in Dara W. Frank et al. (J. Infect. Disease, 2002, Vol. 186, p. 64).

Another feature of the monoclonal antibody of the present invention is to have its epitope in a region from positions 136 to 233 in full-length amino acid sequence of PcrV (SEQ NO: 1). The present inventors have found that an antibody that recognizes this region has stronger activity (cytotoxicity inhibiting activity) than an antibody that recognizes other region. The antibody that recognizes this region is useful for the treatment of infectious diseases because it has strong cytotoxicity inhibiting activity.

Recognition epitope of monoclonal antibody may be identified in the following manner. First, a variety of partial structures of a molecule to be recognized by the monoclonal antibody are prepared. For preparation of partial structures, a method of preparing various partial peptides of the molecule with a known oligopeptide synthesis technique, a method of producing them in or out of host such as *E. coli* by incorporating into a suitable expression plasmid a DNA sequence encoding an objective partial peptide with a gene recombination technique, or the like are known, however, it is general to use combination of these methods for the aforementioned object. For example, after preparing a series of polypeptides shortened in an appropriate length from C terminal or N terminal of antigen protein by using a gene recombination technique well-known by a person skilled in the art, reactivity of monoclonal antibody with these polypeptides is examined and a recognition site is roughly determined.

Thereafter, a variety of oligopeptides of the corresponding part, mutants of the peptide, or the like are synthesized more finely by using an oligopeptide synthesis technique well-known by a skilled person in the art, and determination of epitope is made by examining bindability of a monoclonal antibody containing a prophylactic or therapeutic agent of the present invention as an active ingredient, with these peptides, or by examining competitive inhibiting activity of these peptides to binding between the monoclonal antibody and antigen. As a convenient method for obtaining a variety of oligopeptides, a commercially available kit (For example, SPOTs kit (available from Genosys Biotechnologies, Inc.), or a series of multipin/peptide synthesis kit with a multipin synthesis method (available from Chiron Corporation) may also be used.

Cytotoxicity inhibiting activity may be measured in the following manner. First, a monoclonal antibody for which cytotoxicity inhibiting activity is to be measured is diluted into appropriate concentrations in 2-fold dilution series. Next, cells that are influenced by toxin of *Pseudomonas aeruginosa* or the like (hereinafter, referred to as target cells) are diluted, for example, by using a culture medium for cell culture, to achieve an appropriate number. Concretely, it is preferred to adjust into $3 \times 10^6$ to $5 \times 10^6$ cells/mL when myeloma cells are used, and to adjust to $1 \times 10^6$ to $3 \times 10^6$ cells/mL when leukocyte cells are used. Likewise, *Pseudomonas aeruginosa* cells are also adjusted to $1 \times 10^7$ to $5 \times 10^8$ cfu/mL using, for example, a culture medium. In the presence of the monoclonal antibody, *Pseudomonas aeruginosa* cells and target cells are cultured in the same test tube or well (for example, in vitro condition such as a well on a micro plate) in an appropriate culture condition. The culture condition at this time may be a commonly employed culture condition considered as being suited for growth of cells or bacteria. As for the culture time, optimum condition is appropriately changed depending on the kind of target cells, and for example, about 1 to 3 hour(s) for the case of using myeloma cells, and about 1 to 3 hour(s) for the case of using leukocyte cells are preferred. Taking a well not added with an antibody as a control group, a concentration at which 50% inhibition compared to the control group (effective concentration) is observed is calculated. As for decision of live and death of target cells, although various procedures have been established, for example, measurement of absorbance at an appropriate wavelength (for example, 400 to 500 nm) after addition of a coloring reagent is useful (See Nature Medicine 1999, vol. 5, p. 392-395, for reference).

One feature of the monoclonal antibody of the present invention is to have high affinity with PcrV. Dissociation constant (Kd) which is used as an index of affinity with antibody of monoclonal antibody may be analyzed in various ways. For example, analysis can be readily conducted according to Scatchard method using an antigen labeled with various labeling agents, or a method using a commercially available measurement kit Biacore X (available from Amersham Pharmacia) or a similar kit according to the instruction manual and experimentation protocol attached to the kit. Evaluation of binding activity can be conducted according to ELISA (Enzyme-linked immunosorbent assay), EIA (Enzyme immunoassay), RIA (Radioimmune assay) or fluorescent antibody assay. Dissociation constant (Kd value) determined using such a method is represented in a unit of M (mol). The smaller the dissociation constant of the tested monoclonal antibody, the stronger affinity the tested monoclonal antibody has. As to the monoclonal antibody of the present invention or a part thereof, dissociation constant (Kd) of PcrV is $2 \times 10^{-9}$ (M) or less, preferably $1.5 \times 10^{-9}$ (M) or less, and more preferably $1.2 \times 10^{-9}$ (M) or less.

In the monoclonal antibody of the present invention, preferably, the antibody has immunoglobulin heavy chain variable region, including complementarity determining region: CDR1, thereof amino acid sequence is SFTSYWMH (SEQ ID NO: 15); CDR2, thereof amino acid sequence is INPSNGRTNYNEKFNT (SEQ ID NO: 16); CDR3, thereof amino acid sequence is YGNYVVYYTMDY (SEQ ID NO: 17) and immunoglobulin light chain variable region, including complementarity determining region: CDR1, thereof amino acid sequence is SASTSVSYME (SEQ ID NO: 18); CDR2, thereof amino acid sequence is TTSKLAS (SEQ ID NO: 19); CDR3, thereof amino acid sequence is HQWRNYPFT (SEQ ID NO: 20).

As for the sequence of CDR region, a modified body with addition, insertion, substitution or deletion of one or several amino acid in at least one CDR of the above-described three CDR set may be embraced in the present invention as far as a bioactivity (for example, affinity, cytotoxicity inhibition or the like) requested in the present invention is maintained.

As a preferable aspect of this present invention, humanized version of monoclonal antibody having above described feature can be recited. Humanized monoclonal antibody is obtained by transplanting a complementarity determining region (CDR) of antibody of a mammal other than human, for example, of a mouse, into CDR of human antibody. Therefore, framework region derives from human antibody. Suitable framework can be selected according to documents of Kabat E. A. et al. FR can be selected in such a manner that CDR can form appropriate antigen-binding site. If necessary, amino acid of FR of variable region may be substituted in such a manner that CDR of reconstructed humanized antibody can form appropriate antigen-binding site (Sato, K. et al., Cancer Res. 1993, vol. 53. p. 851). In this case, the above-described steps may be repeated.

General production method for humanized monoclonal antibody is also known (for example WO95/14041 and WO96/02576 etc.). Concretely, DNA sequence, encoding variable region designed to connect CDR of mouse antibody with FR of human antibody, is synthesized by PCR method from several oligonucleotides prepared to have overlapping parts in their terminals (refer to WO98/13388). Obtained DNA is connected to DNA encoding constant region of human antibody and the resultant DNA is incorporated into expression vector. Alternatively, DNA encoding variable region of antibody may be incorporated into expression vector comprising DNA encoding constant region of antibody. To prepare for antibody of the present invention, antibody gene may be incorporated into an expression vector to express under control of an expression control region, for example enhancer/promoter. Further, the host cells are transformed with this expression vector and could thus produce antibody. As host cell, vertebrate cell such as COS cells or CHO cells, procaryotic cell or yeast can be recited.

For expression of antibody gene, heavy chain (H chain) or light chain (L chain) of antibody may be separately incorporated into expression vectors, and a host may be transformed with these expression vectors, or DNA encoding H chain and L chain may be incorporated into a single expression vector to transform a host with the resultant expression vector (see WO94/11523).

Desirable transformants, obtained by methods previously described, can be cultured by the methods known for the skilled person. By this culture, humanized monoclonal antibody against PcrV is produced in the transformants or outside the cells. Medium for the culture can be selected from conventional mediums appropriately depending on the host cell. In the case of above described COS cells, medium such as RPMI-1640, Dulbecco's Modified Eagle Minimum Essential Medium (DMEM), are available and if necessary, the serum ingredients likewise Fetal Bovine Serum (FBS) can be added. The temperature for cultivating the transformants is not restricted, as far as not lowering the ability for producing protein in the cell seriously. Preferably temperatures of 32-42° C. are recited. Most preferably, temperature of 37° C. is recited. As necessary, cultivating can be performed in the atmosphere containing carbon dioxide of 1-10% (v/v).

Fractions containing humanized antibody against PcrV of the present invention, produced in the transformants or outside cells by the methods previously described, can be refined by the heretofore known separation methods. These methods are based on physical property or chemical property of the target protein. Concretely, for example, treatment with protein precipitant, chromatography such as ultrafiltration chromatography, size separation chromatography, adsorption filtration chromatography, ion exchange chromatography, affinity chromatography, or high performance liquid chromatography, dialysis, and combination thereof are available.

According to methods previously described, desirable humanized monoclonal antibody against PcrV can be produced easily in good yield and good purity. Amino acid sequences of variable region of the optimized antibodies are shown as SEQ ID: No. 27 in FIG. 15 and SEQ ID: No. 28 in FIG. 16. These antibodies were constructed by grafting amino acid of whole CDR sequences and partial FR sequences, which are determined for humanization of mouse monoclonal antibody 1F3, into human antibody.

Compared to mouse antibody (m1F3) produced by hybridoma cells, this humanized antibody (h1F3) had equivalent cytotoxicity inhibiting activity. Though humanization of antibody with maintaining activity of the original antibody is usually difficult, the inventors of the present invention were successful to obtain humanized antibody having equivalent activity of the original mouse antibody. Humanized antibody is useful for the purpose for treatment because of its lower antigenicity in human body.

As the humanized antibody of the present invention, human antibody constant region is available. As a preferred human antibody constant region, Cγ can be recited for heavy chain, and for example, Cγ1, Cγ2, Cγ3 and Cγ4 may be used and Cκ or Cλ can be recited for light chain. Further, human antibody C region may be modified to improve its stability of antibody or its productivity. In humanization, available human antibody may be any isotype such as IgG, IgM, IgA, IgE and IgD. As the present invention, IgG is preferable and IgG1 or IgG4 are more preferable.

Humanized monoclonal antibody of the present invention may be conjugated antibody, which is made by conjugating with some molecule such as polyethylene glycol (PEG), radioactive substance, or toxin. These conjugated monoclonal antibodies are obtained by modifying the antibody chemically. Methods for modifying antibody have established in this technical field. Humanized monoclonal antibody of the present invention embraces these conjugated monoclonal antibodies.

Humanized monoclonal antibody of the present invention may be fused with other proteins at its N terminal site or C terminal site (Clinical Cancer Research, 2004, 10, 1274-1281). The skilled person can select proteins for fusion appropriately.

Humanized monoclonal antibody of the present invention may be that of which cytotoxicity inhibiting activity is improved. These antibodies are, for example, fucose-removed antibody, antibody conjugated with bisecting N-acetyl glucosamine via its sugar chain (GlcNAc), or antibody of which binding activity with Fcγ receptor is changed by substitution of amino acid residue of Fc region. These antibodies can be produced by the methods known to the skilled person.

In the present invention, the phrase "part of monoclonal antibody" means a region that is a part of the aforementioned monoclonal antibody of the present invention and has specific bindability to PcrV likewise the monoclonal antibody (hereinafter, also referred to as simply "antibody fragment").

Concretely, Fab (fragment of antigen binding), F(ab')$_2$, Fab', single chain antibody (single chain Fv; hereinafter denoted by scFv), disulfide stabilized antibody (disulfide stabilized Fv; hereinafter denoted by dsFv), dimerized V region fragment (hereinafter, denoted by Diabody), peptide containing CDR, having specific bindability to the human PcrV, can be recited (Expert opinion on therapeutic patents, vol. 6, No. 5, p. 441-456, 1996).

Fab is an antibody fragment having a molecular weight of about 50,000 with antigen binding activity, made up of about a half of N-terminal side of H chain and whole L chain, obtained by degrading with an enzyme papain a peptide part above two disulfide bonds (S—S bond) cross-linking two H chains in hinge region of IgG. Fab used in the present invention may be obtained by treating the monoclonal antibody of the present invention with papain. Alternatively, Fab may be produced by inserting DNA encoding Fab of monoclonal antibody of the present invention into an expression vector for cell and by introducing the vector into a cell to cause expression.

F(ab')₂ is an antibody fragment having a molecular weight of about 100,000 with antigen binding activity, formed by binding two Fab' regions in a hinge part. These Fab' regions are obtained by pepsin degradation below two S—S bonds of hinge region of IgG. The F(ab')₂ used in the present invention may be obtained by treating the monoclonal antibody of the present invention with pepsin. Alternatively, F(ab')₂ may be produced by inserting DNA encoding F(ab')₂ of the monoclonal antibody into an expression vector for cell and by introducing the vector into E. coli, yeast or animal cell to cause expression.

Fab' is an antibody fragment having a molecular weight of about 50,000 with antigen binding activity, obtained by cutting S—S bond between hinges of the aforementioned F(ab')₂. Fab' used in the present invention may be obtained by treating F(ab')₂ of monoclonal antibody of the present invention with a reducing agent, dithiothreitol. Alternatively, Fab' may be produced by inserting DNA encoding Fab' of the monoclonal antibody into an expression vector for cell and by introducing the vector into E. coli, yeast or animal cell to cause expression.

scFv is VH-P-VL or VL-P-VH peptide in which one VH chain and one VL chain are connected using an appropriate peptide linker (hereinafter, denoted by P), and is an antibody fragment having antigen activity. VH and VL contained in scFv used in the present invention may be derived from the monoclonal antibody of the present invention. scFv used in the present invention may be produced by acquiring cDNA encoding VH and VL from hybridoma producing a monoclonal antibody of the present invention, constructing a scFv expression vector, and causing expression by introducing the expression vector into E. coli, yeast or animal cell.

dsFv refers to one obtained by binding polypeptides, in which each one amino acid residue is substituted with a cysteine residue in VH and VL, via S—S bond. The amino acid to be substituted with cysteine residue may be selected based on tertiary structure prediction of antibody according to the method indicated by Reiter et al. (Protein Engineering, 7, 697 (1994)). VH or VL contained in dsFv used in the present invention may be derived from the monoclonal antibody of the present invention. dsFv used in the present invention may be produced by acquiring cDNA encoding VH and VL from hybridoma producing a monoclonal antibody of the present invention, constructing a dsFv expression vector by inserting it into an appropriate expression vector, and causing expression by introducing the expression vector into E. coli, yeast or animal cell.

Diabody is an antibody fragment where a dimer of scFvs having the same or different antigen binding specificity is formed, and is an antibody fragment having bivalent antigen binding activity for the same antigen or two antigen binding activities specific for different antigens. For example, bivalent Diabody that specifically reacts with the monoclonal antibody of the present invention may be produced by acquiring cDNA encoding VH and VL of a monoclonal antibody of the present invention, constructing DNA encoding scFv having a peptide linker of 3 to 10 residues, inserting the DNA into an expression vector for cell, and causing expression of Diabody by introducing the resultant expression vector into E. coli, yeast or animal cell.

Peptide containing CDR includes at least one region of CDR of VH or VL. Plural CDRs may be combined directly or via an appropriate peptide linker. Peptide containing CDR used in the present invention may be produced by acquiring cDNA encoding VH and VL of a monoclonal antibody of the present invention, constructing DNA encoding CDR, inserting the DNA into an expression vector for animal cell, and causing expression by introducing the resultant expression vector into E. coli, yeast or animal cell. Peptide containing CDR may also be produced by chemical synthesis method such as Fmoc method (fluorenyl methyloxycarbonyl method) or tBoc method (t-butyloxycarbonyl method).

A monoclonal antibody of the present invention or a part thereof may be modified insofar as it is suitably used in the present invention. As a modified substance, antibodies bound to various molecules including polyethylene glycol (PEG) or the like may be used. Modification made on antibody may be modification by introduction of chemical bond, or may be modification made on amino acid sequence of the antibody. A monoclonal antibody of the present invention or a part thereof also embraces these antibody modified substances. For obtaining such antibody modified substances, the obtained antibody may be modified. These techniques have been already established in the art.

In another aspect, the present invention provides polynucleotide encoding heavy variable region or light variable region, of humanized monoclonal antibody (h1F3) of the present invention. Preferably, the polynucleotide of the present invention has base sequence of any of SEQ ID: 29 or 30. The present invention also embraces polynucleotide, which can hybridize with the said polynucleotide in a stringent condition and encodes antibody having equivalent activity with antibody of the present invention.

The polynucleotide of the present invention is polymer consisting of nucleotide such as several deoxyribonucletic acid (DNA) or ribonucletic acid (RNA), so far as encoding antibody of the present invention. These may include bases other than natural products. The polynucleotide of the invention can be available for producing antibodies in a manner of genetic technology. The polynucleotide of the invention can be also useful as probe for the screening of antibodies having equivalent activity with the antibody of the present invention. So, by using as probe polynucleotide encoding antibody of the present invention or a part thereof, applying technique such as hybridization or gene amplification technique, for example, PCR, DNA which can hybridize with said polynucleotide in the stringent condition and encodes antibody having equivalence activity with antibody of the present invention, is obtainable. Such these DNA are also embraced in the polynucleotide of the present invention.

Hybridization technique (Sambrook, J et al., Molecular Cloning 2nd ed., 9.47-9.58, Cold Spring Harbor Lab. press, 1989) is the well-known art for the skilled person. The condition for hybridization is for example, low-stringent condition. The low-stringent condition means washing step after hybridization is carried on under, for example, 0.1×SSC containing 0.1% SDS at 42° C., preferably 0.1×SSC containing 0.1% SDS at 50° C. More preferable hybridization condition is high-stringent. High-stringent condition means for example, under 5×SSC containing 0.1% SDS at 65° C. Under these conditions, with higher temperature, higher similarity polynucleotide is expected to be obtained efficiently. As a factor affecting stringency for hybridization, several factors such as temperature, or salt concentration, are recited. The skilled person could select these factors appropriately and could have a similar stringency.

Antibodies, functionally equivalent to antibody of the present invention, have generally high similarity in amino acid sequence. These antibodies are encoded by polynucleotide, which are obtained with above described hybridization or gene amplification techniques. The antibodies, which are functionally equivalent to the antibody of the present invention and have high similarity in amino acid sequence of the antibodies, are embraced in the present invention. High similarity means the similarity of at least more than 50% in amino acid sequence, preferably the similarity of 75%, and more preferably the similarity of 85% and 95%. To determine the similarity of the polypeptide, algorithm described in the document (Wilbur, W. J. and Lipman, D. J. Proc. Natl. Acad. Sci. USA (1983) 80, 726-730) is available.

A monoclonal antibody of the present invention and a part thereof is useful as a pharmaceutical composition. Therefore, a pharmaceutical composition containing a monoclonal antibody of the present invention and a part thereof may be administered systemically or topically by in an oral or parenteral route. For parenteral administration, for example, intravenous injection such as drip infusion, intramuscular injection, intraperitoneal injection, subcutaneous injection, intranasal administration, inhalation or the like can be selected. However, since it is known that Pseudomonas aeruginosa will inflict damage particularly on lung epithelial cell and macrophage of pulmonary alveolus by respiratory tract infection (T. Sawa et al., Nature Medicine, 1999, vol. 5, p. 392), intranasal administration and inhalation are desired.

A pharmaceutical composition of the present invention is administered for therapy of a patient suffering from cystic fibrosis or infection by Pseudomonas aeruginosa. For example, effective dose is selected in the range of 0.01 mg to 100 mg per 1 kg of body weight per one time. Alternatively, a dose of 1 to 1000 mg, preferably a dose of 5 to 50 mg per a patient may be selected. However, a dose of the pharmaceutical composition containing the monoclonal antibody of the present invention or a part thereof is not limited to these doses. Administering duration may be appropriately selected depending on the age, symptom or the like of the patient. The pharmaceutical composition of the present invention may also include a pharmaceutically acceptable carrier or additive as well depending on the route of administration.

Examples of such carrier and additive include water, pharmaceutically acceptable organic solvent, collagen, polyvinyl alcohol, polyvinylpyrrolidone, sodium alginate, water-soluble dextran, pectin, methyl cellulose, ethyl cellulose, casein, diglycerin, propylene glycol, polyethylene glycol, Vaseline, human serum albumin (HSA), mannitol, sorbitol, lactose, and surfactants permitted as a pharmaceutical additive. An additive for use is appropriately selected or combined from the above depending on the dose form, but, it is not limited thereto.

The method for preparation of mouse monoclonal antibody against PcrV will be explained by the way of the following Reference Examples.

Reference Example 1

Preparation of Recombinant Mab166

For executing a comparative experiment, Mab166 (Japanese patent Application No. 2005-500250 or the like) was prepared as a recombinant antibody.

First, mRNA is extracted from hybridoma that produces an antibody classified into a subclass IgG2a, and constant regions of H chain and L chain were cloned by RT-PCR method. Each fragment amplified by PCR was inserted into NheI-NotI site of pcDNA3.1 (+) vector (available from Invitrogen Corporation), and a multi-cloning site was further incorporated for allowing a DNA fragment of variable region part to be inserted.

Next, after splitting gene sequence of H chain and L chain of Mab166 variable region part into four, sense DNA and antis-sense DNA of these were synthesized, and annealed. Fragments after annealing were caused to bind by DNA ligase, and cloning was made at MfeI-BlpI region for H chain, and at EcoRV-BsiWI region for L chain.

Vectors of H chain and L chain having identified base sequences were introduced into HEK 239T cell by using Lipofectamine 2000 (available from Invitrogen Corporation), and after 48 hours, a cell culture supernatant was collected. From the collected cell supernatant, recombinant Mab166 was purified through Protein-G (available from PIERCE) column.

Reference Example 2

Preparation of Antigen

Chromosome DNA of Pseudomonas aeruginosa standard strain PAO1 provided from Tokai University, Japan, was extracted, and gene encoding PcrV protein (SEQ ID NO: 2) was amplified by PCR using the DNA as a template. A recognition site of restriction enzyme SphI was provided in 5'-side primer and a recognition site of restriction enzyme HindIII was provided in 3'-side primer, (SEQ ID NOs: 3, 4), and in insertion into an expression vector a design was made so that cysteine is inserted between histidine tag and start codon for biotin labeling. The amplified PCR fragment was cloned into pWE30 vector (available from GE healthcare) at SphI and HindIII sites. After sequencing, the vector was introduced into E. coli JM109 to obtain recombinant E. coli (PcrV-JM109). PcrV-JM109 was cultured in 500 mL of LB/Ampicillin liquid culture medium at 37° C., and when OD600 reached 0.5, 200 µl of 0.1M IPTG was added. After culturing at 37° C. for additional 1.5 hours, bacterial cells were centrifuged, and added with 15 mL of buffer A (25 mM Tris-HCl (pH 8.0), 0.5 M NaCl, 2 mM $MgCl_2$) containing 0.5% lysozyme (available from Sigma). After the incubation at 0° C. for 30 minutes, cells were sonicated. Following centrifugation, a soluble fraction was obtained, subjected to His-Bind Columns (available from Novagen), and then eluted with buffer B (20 mM phosphate buffer (pH 7.4), 500 mM NaCl) containing 200 mM imidazole. The final elution fraction was dialyzed against 10 mM phosphate buffer (pH 7.4) to replace the buffer.

Biotin Labeling of Antigen

PcrV protein expressed and purified as described above was allowed to react in a mercapto ethylamine solution of a final concentration of 10 mM at 37° C. for 150 minutes to reduce cysteine residue. PEO-maleimide activated biotin (available from PIERCE) was added in an amount of 20-fold by molar ratio with respect to reduced SH groups, and allowed to react overnight at 4° C., and then dialysis was conducted to remove unreacted biotin.

Immunization with Antigen

Each 20 µg of purified PcrV antigen was intraperitoneally immunized with complete Freund's adjuvant to seven Balb/c female mice aged at 4 weeks. Booster immunization was performed by administering 20 µg of PcrV with incomplete Freund's adjuvant after 14 days and 35 days. Further, final immunization was conducted after 77 days by intraperitoneal administration of 20 µg of PcrV and tail vein administration of 10 µg of PcrV.

Preparation of Hybridoma

Spleen was extirpated after 3 days from the final immunization, and spleen cells were collected. A spleen cell and a mouse myeloma cell (p3×63-Ag8.U1, Tokyo mass research laboratory) were fused by using 50% polyethylene glycol 4000, and selected in a culture medium containing hypoxanthine, aminopterin and thymidine.

Selection of PcrV Antibody

After 8 days from cell fusion, specific antibody producing cells were screened. Immunoassay used in screening was as follows. Each well of a 96-well microtiter plate (available from Nunc) was added with 200 μL of tris buffer (50 mM Tris-HCl, pH7.5) containing 2 μg of anti-mouse IgG antibody (available from Shibayagi) and immobilized for 16 hours at 4° C. These wells were washed twice with 300 μl of washing solution (saline containing 0.1% Tween 20), then added with 300 μl of BlockAce (available from Dainippon Sumitomo Pharma Co., Ltd.) and left for two hours at room temperature. After washing each well twice with 300 of washing solution, 50 μl of hybridoma culture supernatant was diluted with 150 μl of buffer C (50 mM tris buffer, pH 7.6 containing 0.9% sodium chloride, 0.05% sodium azide, 0.5% bovine serum albumin, 0.01% Tween80, and 25 μM Diethylenetriamine-N,N,N',N'',N''-pentaacetic acid) and added to each well, and allowed to react overnight at 4° C. After washing three times with 300 μl of washing solution, 200 μl of buffer C containing 10 ng of Eu-Labeled Streptavidin (available from PERKIN ELMER) and 25 ng of biotin-labeled PcrV was added, and allowed to react for 1 hour at room temperature. After the reaction, washing three times with 300 μl of washing solution, and 200 μl of enhancement reagent (1.39 g/l potassium phthalate, 19.3 mg/l of Tri-n-octylphosphine oxide, 4.59 mg/l of 2-naphthoyltrifluoroacetone, 1.0 g/l of Triton-X100, 6.0 g/l of acetic acid) was added, and time-resolved fluorescence was measured.

From the result of screening, 20 clones of hybridoma which exhibited strong affinity with recombinant PcrV were selected, and cytotoxicity inhibition activity by *Pseudomonas aeruginosa* was examined according to Example 4. As a result, cytotoxicity inhibiting activity was observed in 10 clones, and these clones were then cloned twice by limiting dilution method, and thus hybridoma cells were selected. From the obtained 10 clones, 4 clones exhibited high cytotoxicity inhibition activity were selected, and named 1F3, 2A4, 6F5, and 7A7, respectively. For these antibodies, subclass of antibody was determined using mouse monoclonal antibody isotyping ELISA kit (available from BD Biosciences), and it was found that 1F3 was IgG2a, 2A4 was IgG2b, 6F5 was IgG2a, 7A7 was IgG2a.

Hybridomas cells that produce monoclonal antibodies 1F3 and 2A4 were deposited with National Institute of Advanced Industrial Science and Technology, International Patent Organism Depositary (Center No. 6, 1-1-1, Higashi, Tsukuba-shi, IBARAGI, JAPAN) on Jan. 15, 2009, under the accession numbers of FERM ABP-11805 and FERM ABP-11806, respectively.

Reference Example 3

Binding Activity of Antibody

For measuring binding activity of antibodies (1F3, 2A4, 6F5, 7A7), competitive immunoassay was performed. Each well of a 96-well microtiter plate (available from Nunc) was added with 100 μl of tris buffer (50 mM Tris-HCl, pH7.5) containing 1.5 μg of anti-mouse Fc antibody (available from Jackson ImmunoReseach) and immobilized for 16 hours at 4° C. These wells were washed twice with 300 μl of washing solution, then added with 300 μl of BlockAce (available from Dainippon Sumitomo Pharma Co., Ltd.) including 10% sucrose and left for two hours at room temperature to achieve blocking (anti-mouse IgG antibody solid-phased plate). After washing twice with 300 μl of washing solution, 2 ng/well of each antibody and non-labeled PcrV at five concentrations in 10-fold dilution series from 500 ng/well were added. Then, 5 ng/well of biotinylated PcrV was added and allowed to react overnight. After washing four times with 300 μl of washing liquid and adding with 100/well of Enhancement Reagent (available from Wallac), time-resolved fluorescence was measured after stirring for 1 minute. As a result, 1F3, 2A4, 6F5 and 7A7 showed stronger binding activity against PcrV than Mab166 (FIG. 1).

Next, affinity of 1F3, 2A4, 6F5, 7A7 and Mab166 with PcrV was determined by surface plasmon resonance analysis. Anti-mouse antibody was immobilized on a CM5 sensor chip by using Mouse Antibody Capture Kit (available from BIACORE). Sequentially, each PcrV antibody was captured. The recombinant PcrV was loaded on BIAcore T100 instrument with the sensor chip to determine the affinity.

As a result, every clone showed higher affinity than Mab166 as evidenced from the affinity of $3.7 \times 10^{-10}$ for 1F3, the affinity of $3.5 \times 10^{-10}$ for 2A4, the affinity of $1.1 \times 10^{-10}$ for 6F5, and the affinity of $1.1 \times 10^{-9}$ for 7A7, in contrast to the affinity of $3.0 \times 10^{-9}$ for Mab166 (FIG. 2).

Reference Example 4

Sandwich Immunoassay with Mab166

In order to prove that 1F3, 2A4, 6F5 and 7A7 have a different epitope from that of Mab166, sandwich immunoassay between each antibody and Mab166 was examined.

First, Mab166 was labeled with biotin. One hundred μg of Mab166 and 7.853 μg of NHS-PEO4 Biotin (available from PIERCE) were mixed in 0.1M PBS (pH 7.4), and allowed to react for 2 hours on ice. Thereafter, gel chromatography (G2000SW column (available from TOSOH)) was carried out to remove unreacted biotin from the reaction solution.

Sandwich immunoassay was performed as follows. Each well of a 96-well microtiter plate (available from Nunc) was added with 100 μl of PBS (−) solution each containing 500 μg of PcrV antibody (1F3, 2A4, 6F5, 7A7) and immobilized for 16 hours at 4° C. These wells were washed once with 300 μl of a washing solution (saline containing 0.01% Tween 20), then added with 300 μl of BlockAce (available from Dainippon Sumitomo Pharma Co., Ltd.) and left for two hours at room temperature to achieve blocking. After washing each well twice with 300 of washing solution, 100 μl of Assay Buffer (available from Wallac) containing 50 μg of PcrV and 50 ng of biotin-labeled Mab166 was added and allowed to react overnight at 4° C. After washing four times with washing solution, 100 μl of Assay Buffer containing 50 ng of Eu-Labeled Streptavidin (available from Wallac) was added, and allowed to react for 1 hour at room temperature. After washing three times with washing solution and adding 100 μl of Enhancement Reagent, stirring for 1 minute, and then time-resolved fluorescence was measured.

As a result, sandwich immunoassay was possible between any of 1F3, 2A4, 6F5 and 7A7 and Mab166, so that it was revealed that the present antibodies had a different epitopes from that of Mab166 (FIG. 3).

Reference Example 5

Measuring the Cytotoxicity Inhibition Activity

For 1F3, 2A4, 6F5 and 7A7, cytotoxicity inhibiting activity was measured. The method is as follows.

First, 1F3, 2A4, 6F5, 7A7 was diluted in 2-fold dilution series from 32 μg/ml, and 10 was dispensed into each well of 96-well microplate. Next, mouse myeloma cell P3U1 (from ATCC) was adjusted to 5×10⁶ cells/ml or human leukocyte cell-line U937 (from ATCC) cell was adjusted to 1×10⁶ cells/ml in a cell culture medium (RPMI1640 containing sodium hydrogen carbonate, and not containing L-glutamine and phenol red (available from Sigma)), and each 100 μl of cell suspension was added to the 96-well microplate. Further, Pseudomonas aeruginosa strain SR24 cultured overnight in Cation-adjusted Mueller Hinton Broth (Difco) was adjusted to 1×10⁸ cfu/ml in a cell culture medium, and added in an amount of 10 μl/well, and cultured for 3 hours at 37° C. in the presence of 5% $CO_2$. After stirring for 3 hours, each 10 μl of WST-8 (available from Kishida Chemical Co., Ltd.) was added, and cultured at 37° C. in the presence of 5% $CO_2$ for 3 hours for the case of myeloma cell P3U1, or for 1 hour for the case of U937 cell. After completion of culture, absorbance 450 nm was measured.

Figure 5:
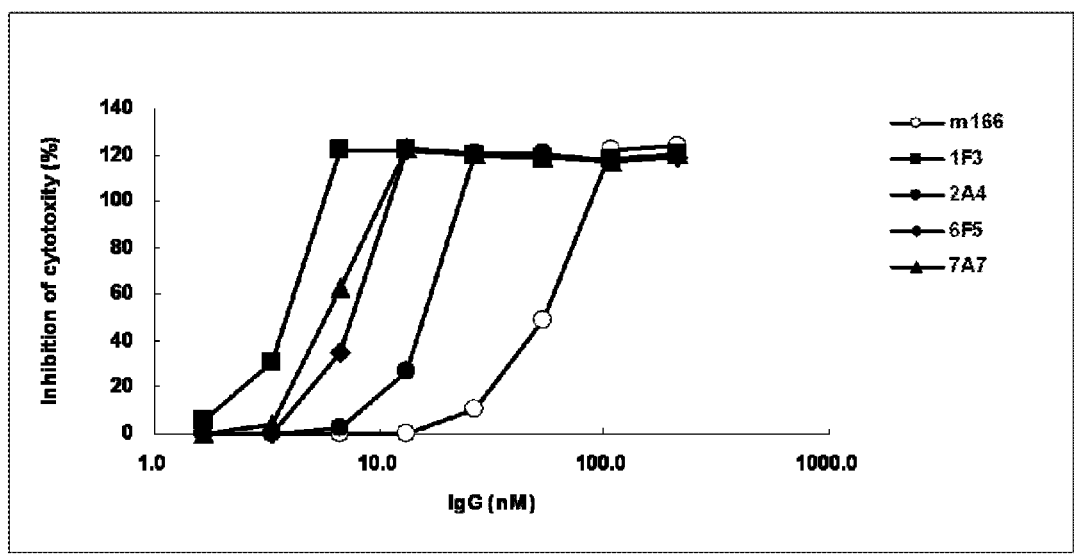
FIG. 5 shows inhibiting effects of PcrV antibodies (1F3, 2A4, 6F5, 7A7 and Mab166) on cytotoxicity to myeloma cells P3U1 of *Pseudomonas aeruginosa* strain SR24.

As a result, when leukocyte U937 cell was used, cytotoxicity inhibiting activity (IC50) was 5.3 nM for 1F3, 20.7 nM for 2A4, 12.7 nM for 6F5, and 14.7 nM for 7A7 in contrast to higher than 213 nM for Mab166, and when myeloma cell U3P1 was used, cytotoxicity inhibiting activity (IC50) was 4.0 nM for 1F3, 16 nM for 2A4, 7.3 nM for 6F5, and 6.0 nM for 7A7 in contrast to 54 nM for Mab166. That is, 1F3, 2A4, 6F5 and 7A7 had higher cytotoxicity inhibition activity for both cells than Mab166 which has been previously described (Frank et al., The Journal of Infectious Diseases, 2002, vol. 186, p. 66) (FIG. 4 and FIG. 5).

Reference Example 6

Preparation of Truncated PcrV

Truncated PcrV (136-233) was prepared in the following manner.

A fragment amplified by PCR with 5'-side primer GCTC-GAGGATCCCAAGGCGCTGACCGC (SEQ ID NO: 5) and 3'-side primer GTTAAGCTTCTCGAAGGGGTACTC (SEQ ID NO: 6) by using pQE30-PcrV being a PcrV antigen protein expression plasmid as a template was treated with restriction enzymes BamHI and HindIII, and inserted into pET32b (available from Novagen). After sequencing, the vector was introduced into E. coli strain BL21-DE3 to obtain recombinant E. coli (truncated PcrV-BL21). This expression strain was pre-cultured for a whole day and night at 37° C. in 2 ml of LB/Ampicillin liquid culture medium. Two mL of pre-culture liquid was added into 500 ml of LB/Ampicillin liquid culture medium and cultured at 37° C., and when OD600 reached 0.5, the culture liquid was kept still for 30 minutes on ice. IPTG was added to final concentration 0.75 mM, and cultured at 160 rpm in a rotary shaker incubator at 15° C. for a whole day and night. Bacterial cells were collected by centrifuging the culture liquid at 4° C., ×5000 g for 30 minutes. The supernatant was removed, and 10 ml of Buffer X (25 mM Tris-HCl (pH7.5), 150 mM NaCl, 2 mM $MgCl_2$) containing 0.1% lysozyme (available from Sigma) was added to the pellet and suspended, left still on ice for 1 hour, and then sonicated under cooling on ice. Then a soluble fraction was applied to a Ni-NTA agarose filled column (Quiagen), and eluted with Buffer Y (25 mM Tris-HCl (pH 7.5), 150 mM NaCl, 200 mM Imidazole). The eluted fraction was dialyzed with 10 mM phosphate buffer (pH 7.4).

Determination of Epitope Region

Figure 6:
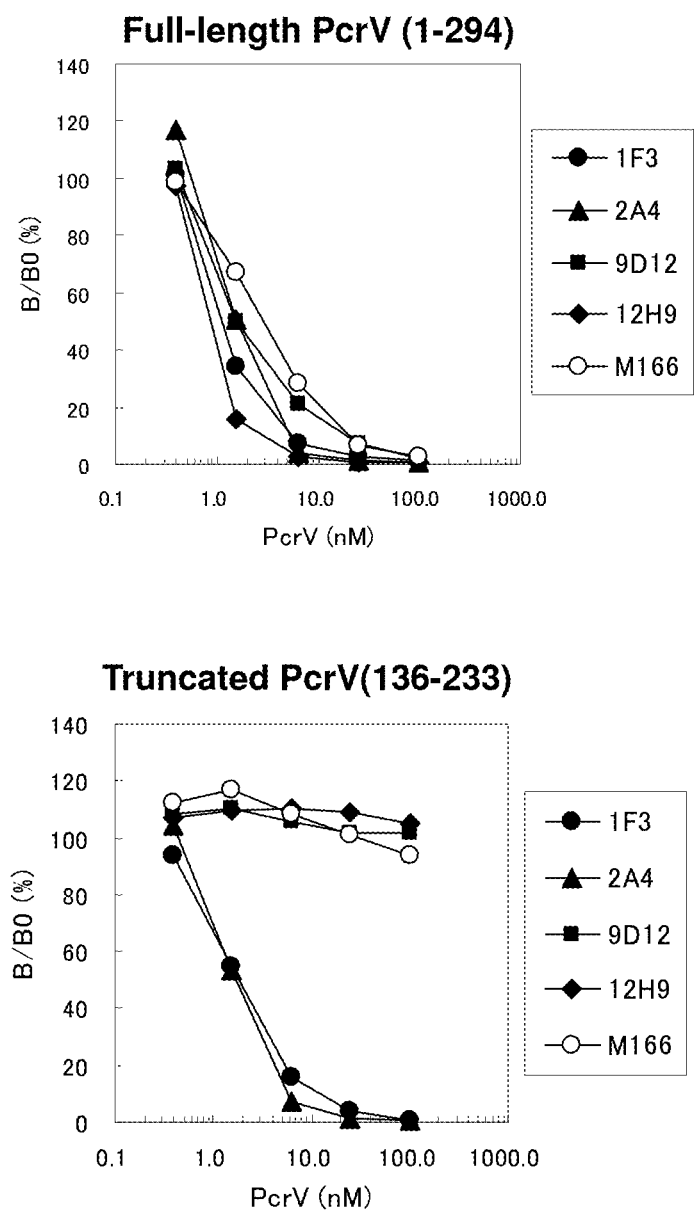
FIG. 6 shows curves in which biotin-labeled PcrV is substituted by non-labeled full-length PcrV and truncated PcrV in PcrV antibodies (1F3, 2A4, 9D12, 12H9 and Mab166).

Each well of a 96-well microtiter plate (available from Nunc) was added with 150 μl of tris buffer (50 mM Tris-HCl, pH 7.5) containing 1.5 μg of anti-mouse IgG Fc antibody (available from Jackson ImmunoResearch) and immobilized for 16 hours at 4° C. These wells were washed twice with 300 μl of a washing solution (saline containing 0.01% Tween 20), then added with 300 μl of blocking solution (500 mM Tris-Hcl pH7.5, 2% BlockAce (available from Dainippon Sumitomo Pharma Co., Ltd.), 10% sucrose) and left for two hours at room temperature to block each well (anti-mouse IgG antibody immobilized plate). After washing each well once with 300 μl of washing liquid, each well was added with 50 μl of PcrV antibody solution diluted into a concentration of 80 ng/ml with Buffer C (50 mM tris buffer containing 0.9% sodium chloride, 0.05% sodium azide, 0.5% bovine serum albumin, 0.01% Tween 80, and 25 μM Diethylenetriamine-N,N,N',N",N"-pentaacetic acid, pH 7.6), followed by 50 μl of Eu-Labeled Streptavidin (available from PERKIN ELMER) solution diluted into a concentration of 200 ng/ml with Buffer C, 100 μl of truncated PcrV protein diluted in a given concentration with DELFIA Assay Buffer and allowed to react at 4° C. overnight. After washing three times with 300 μl of washing solution, 200 μl of an enhancement reagent (1.39 g/l potassium phthalate, 19.3 mg/l Tri-n-octylphosphine oxide, 4.59 mg/l 2-naphthyoyltrifluoroacetone, 1.0 g/l Triton-X100, 6.0 g/l acetic acid) was added, and time-resolved fluorescence was measured (FIG. 6).

As a result, PcrV antibodies 1F3, 2A4, 9D12, 12H9, and m166 of KaloBios Pharmaceuticals, Inc. used as a reference example, exhibited reactivity with full-length PcrV (1-294). On the other hand, while 1F3 and 2A4 showed reactivity with PcrV (136-233), m166, as well as 9D12 and 12H9 lacking neutralizing activity, did not show reactivity.

Figure 7:
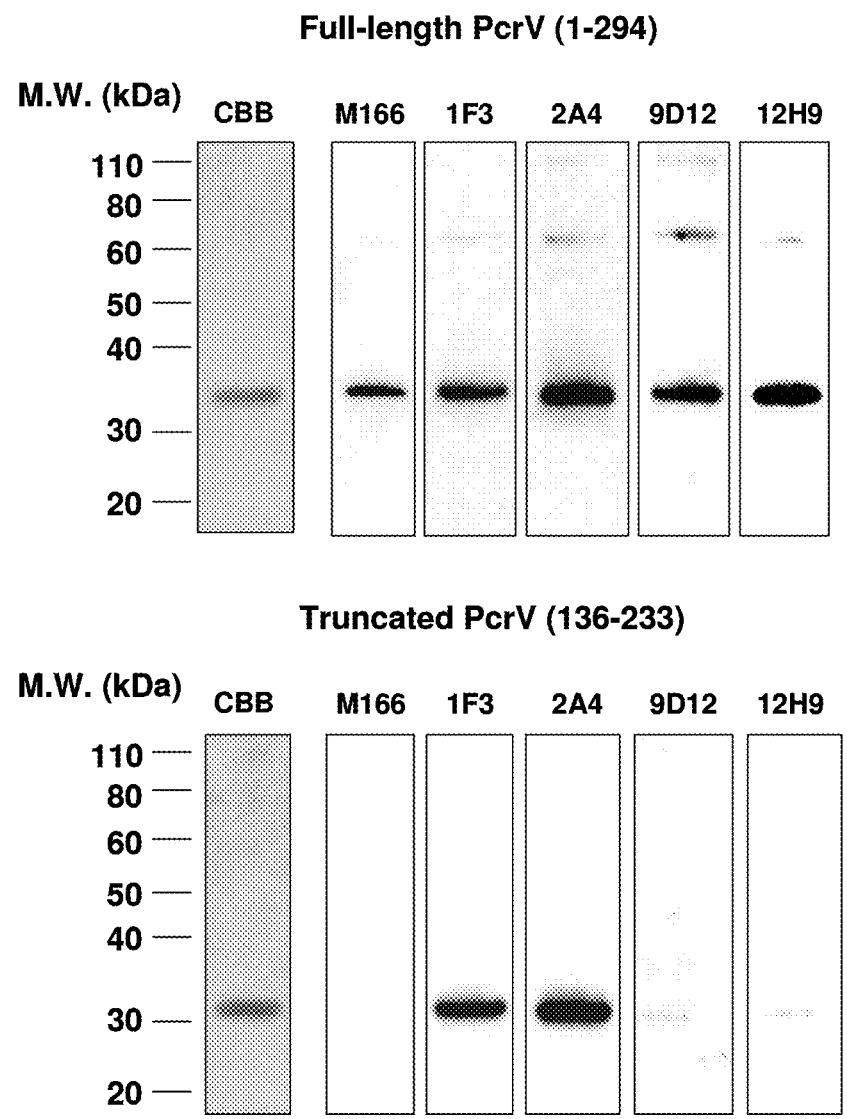
FIG. 7 shows reactivity with full-length PcrV and truncated PcrV in PcrV antibodies (1F3, 2A4, 9D12, 12H9 and Mab166) in Western blotting.

Binding analysis by Western blotting was also conducted. Purified recombinant PcrV protein was applied to SDS-PAGE, and then transferred to PVDF membrane. The transferred membrane was blocked with Block Ace (available from Dainippon Sumitomo Pharma Co., Ltd.) at room temperature for 2 hours under shaking. PcrV antibody solution diluted into 1 μg/mL was added to the membrane, allowed to react overnight at 4° C., and then washed with washing buffer B (10 mM phosphate buffer (pH 7.4), 0.05% Tween 20). As secondary antibody, labeled anti-mouse IgG antibody (available from GE Healthcare) solution was added to the membrane, and allowed to react for 2 hours at room temperature. Thereafter, the membrane was washed with washing buffer B, and the signal was detected by ECL Plus Western Blot Detection System (available from GE Healthcare) and visualized by LAS-1000 (available from FUJIFILM) (FIG. 7). While PcrV neutralization antibodies 1F3 and 2A4 reacted with both of full-length PcrV and truncated PcrV, m166 as well as 6F5 and 7A7 reacted only with full-length PcrV, and did not react with truncated PcrV.

This demonstrated that epitope region of PcrV neutralization antibodies 1F3 and 2A4 was a region corresponding to amino acid residues 136-233, and m166, 6F5 and 7A7 did not exclusively have an epitope region corresponding to amino acid residues 136-233.

Reference Example 7

Correlation Between Specific Region of PcrV Protein and Strength of Cytotoxicity Using full-length PcrV protein (SEQ ID NO: 1) and truncated PcrV protein (having amino acid sequence corresponding to positions 136 to 233 in SEQ ID NO: 1), suppression test of cytotoxicity inhibiting activity in 1F3, 2A4 and m166 were conducted in the following manner.

First, 1F3, 2A4 and m166 were diluted by serial doubling dilution starting with 200 nM, 200 nM and 400 nM, respectively, and 10 μL of these antibodies were added to the 96-well plate. In this test, the test concentration range of 1F3, 2A4 and m166 were adjusted to 1.56-6.25 nM, 6.25-25 nM and 50-200 nM, respectively. For each test concentration range, each 10 μl of full-length PcrV protein or truncated PcrV protein in molar ratios of 30, 10, 3, 1 and 0.3 folds was added to 96-well plate, and kept still for 30 minutes at room temperature. Next, myeloma cell P3U1 was prepared into $5 \times 10^6$ cells/ml in cell culture medium (RPMI1640 containing sodium hydrogen carbonate, and not containing L glutamine and phenol red (available from Sigma)), and each 70 μl was added to the 96-well microplate. Further, a bacterial liquid of *Pseudomonas aeruginosa* strain SR24 cultured overnight in Mueller Hinton Broth (Difco) adjusted to be $1 \times 10^8$ cfu/mL with a cell culture medium was added in an amount of 10 μl/well, and cultured for 3 hours at 37° C. in the presence of 5% $CO_2$. After lapse of 3 hours, each 10 μl of WST-8 (available from Kishida Chemical Co., Ltd.) was added, and cultured at 37° C. in the presence of 5% $CO_2$ for 3 hours. After completion of culture, absorbance was measured at a wavelength of 450 nm.

As a result, when PcrV protein was not added, 1F3 and 2A4 exhibited higher cytotoxicity inhibition activity than m166. On the other hand, when full-length PcrV protein was added, the inhibition effects of all anti-PcrV antibodies were suppressed in a PcrV dose-dependent manner (FIG. 8). When truncated PcrV protein was added, although the inhibition activities of 1F3 and 2A4 were also suppressed in a dose-dependent manner, the inhibition activity of m166 which does not have the epitope did not change (FIG. 9).

From these results, it can be considered that antibodies recognizing an epitope in amino acid residues 136-233 (1F3 and 2A4) have higher cytotoxicity inhibition activity than antibodies not recognizing the epitope (m166). In other words, it can be concluded that cytotoxicity inhibiting activity depends on the epitope region recognized by PcrV antibody, and the antibody reacts only with 136-233 region of PcrV protein has a strong neutralizing activity.

Reference Example 8

Analysis of Amino Acid Sequence of Mouse Monoclonal Antibody Against Human PcrV (1F3 and 2A4)

From the established hybridoma cells, RNA was extracted using RNeasy Mini Kit (available from QIAGEN). From 1 μg of extracted RNA, DNA fragment was amplified using 5'RACE System for Rapid Amplification of cDNA Ends, Version 2.0 (available from Invitrogen). At this time, primers used for synthesis of cDNA were TAGAGTCACCGAG-GAGCCAGTTGT (SEQ ID NO: 7) for 1F3, and TCCA-GAGTTCCAAGTCACAGTCAC (SEQ ID NO: 8) for 2A4. Primers used in 5'RACE method were AGGGGCCAGTG-GATAGACCGATGGGGCTGT (SEQ ID NO: 9) for 1F3, and AGGGGCCAGTGGATAGACTGATGGGGGTGT (SEQ ID NO: 10) for 2A4. The amplified fragments were cloned by TOPO TA Cloning Kit (available from Invitrogen), and sequenced by Applied Biosystems 3130 Genetic Analyzer (available from Applied Biosystems). Analytical result is shown in FIG. 10 for 1F3 and in FIG. 11 for 2A4. As a result of searching homology of amino acid sequence of a variable region by using antibody amino acid database, Sequence of Proteins of Immunological Interest (US Dept. Health and Human Services, 1983) produced by Kabat, complementarity determining region in heavy variable region of 1F3 is SFTSY-WMH (SEQ ID NO:15), INPSNGRTNYNEKFNT (SEQ ID NO:16) and YGNYVVYYTMDY (SEQ ID NO:17): that in light variable region is SASTSVSYME (SEQ ID NO:18), TTSKLAS (SEQ ID NO:19), and HQWRNYPFT (SEQ ID NO:20). As a result of searching in a similar manner, complementarity determining region in heavy variable region of 2A4 is SITSDYAWN (SEQ ID NO:21), YITYNGDTSYNPSLKS (SEQ ID NO:22) and SRNYYGAWFAY (SEQ ID NO:23): that in light variable region is KASQYVGTTVA (SEQ ID NO:24), RASTRHT (SEQ ID NO:25) and QQYCSSPLT (SEQ ID NO:26).

The present invention will be concretely explained by way of the following non-limitative Examples. As a preparation technique of antibody, methods described in Immunochemistry in Practice (Blackwell Scientific Publications) were used unless otherwise specified. As a gene engineering technique, methods described in Molecular Cloning: A Laboratory Manual, 2nd Edition (Cold Spring Harbor Laboratory) were used unless otherwise specified.

Example 1

(1) Humanization of Mouse Monoclonal Antibody 1F3

For humanization of the mouse monoclonal antibody (1F3) prepared as described above, CDRs from a mouse antibody were grafted into the human germline acceptor sequences.

Specifically, IgBLAST (http://www.ncbi.nlm.nih.gov/igblast/) program was used to search for a human germline acceptor sequence showing the highest homology with the amino acid sequence of the V-gene region of each of the heavy and light chains of the mouse antibody. For the J-gene region, a highly homologous sequence to the DNA sequence of the mouse antibody was selected from IMGT (http://imgt-.cines.fr/).

As a result of the search, IMGT gene name; IGHV1-46*01 was obtained as the antibody gene sequence that is derived from a human germline acceptor sequence and shows the highest homology with the V-gene region of the heavy chain of the mouse antibody, and IMGT gene name; IGHJ6*01 as the antibody gene sequence that is derived from a human germline acceptor sequence and shows the highest homology with the J-gene region; these sequences were used as the human framework sequence for grafting the heavy chain. In a similar manner, IMGT gene name; IGKV1-9*01 was obtained as the antibody gene sequence that is derived from a human germline acceptor sequence and shows the highest homology with the V-gene region of the light chain of the mouse antibody, and IMGT gene name; IGKJ2*02 as the antibody gene sequence that is derived from a human germline acceptor sequence and shows the highest homology with the J-gene region; these sequences were used as the human framework sequence for grafting the light chain.

Subsequently, the heavy chains CDRH1, CDRH2 and CDRH3, and the light chains CDRL1, CDRL2 and CDRL3 of the mouse antibody were defined by the amino acid sequence numbering according to the Kabat Numbering (Wu, T. T. and Kabat, E. A., J. Exp. Med. August 1; 132(2):211-50. (1970)). These CDR regions were grafted into the human framework sequences, which were then designed as a template humanized antibody. The difference between the template humanized antibody thus designed and the amino acid sequence of the mouse antibody was confirmed at amino acid sequence number H5, H7, H11, H12, H20, H38, H40, H48, H66, H67, H69, H71, H75, H78, H81, H83, H87, H93, H94, H108, L1, L3, L9, L10, L11, L15, L17, L18, L19, L21, L40, L42, L43, L46, L70, L71, L72, L78, L79, L80, L83, L85, and L100 according to the Chothia Numbering (Chothia, C. and Lesk, A. M., J. Mol. Biol., 196:901-917, Chothia, C. et al., Nature, 342: 877-883. (1989)).

To identify the sites of somatic mutation in the mouse antibody, the amino acid sequence of the V-gene region of each of the heavy and light chains of the mouse antibody was searched using IgBLAST and, as a result, Gene name; J558.33 and Gene name; IGKV4-80*01 were obtained as the most homologous heavy and light chain sequences, respectively. The amino acid sequence of the D-gene region of the heavy chain of the mouse antibody was searched using IgBLAST, and Gene name; IGHD2-1*01 was obtained as the most homologous heavy chain sequence. The DNA sequence of the J-gene region of each of the heavy and light chains of the mouse antibody was searched using IMGT, and IMGT gene name; IGHJ4*01 and IMGT gene name; IGKJ4*01 were obtained as the most homologous heavy and light chain sequences, respectively. These mouse germline sequences were compared with the mouse antibody, and residues with different side chains were defined as the sites of somatic mutation, among which H93, H94, L9 and L46 were confirmed as having different side chains between the mouse antibody and the template humanized antibody.

H71 and H94 were confirmed as the canonical side chains (http://www.bioinf.org.uk/abs/chothia.html) differing between the mouse antibody and the template humanized antibody. Among the side chains differing between the mouse antibody and the template humanized antibody, those located in the Vernier zone (Foote et al., J. Mol. Biol., 224.487 (1992)) were H48, H67, H69, H71, H78, H93, H94, L46 and L71. No interchain packing residue differing between the mouse antibody and the template humanized antibody was identified. Taken these results together, we designed a mutant humanized antibody in which the amino acid side chains at H48, H67, H69, H71, H78, H93, H94, L9, L46 and L71 of the template humanized antibody are all replaced with those from the mouse antibody (backmutations). DNA sequences were designed in which the sequence of the human IgG4Pro constant region is conjugated as the constant region sequence of the heavy chain and the sequence of the human Igkappa constant region is conjugated as the constant region sequence of the light chain for the variable regions of the template humanized antibody designed above (FIG. 12; Template) and the mutant humanized antibody (FIG. 12; Backmutation). Each of the DNA sequences was used to construct a plasmid expressing the heavy chain of the template humanized antibody (FIG. 13; HT), a plasmid expressing the light chain of the template humanized antibody (FIG. 13; LT), a plasmid expressing the heavy chain of the mutant humanized antibody (FIG. 13; HB), or a plasmid expressing the light chain of the mutant humanized antibody (FIG. 13; LB), according to the method described below.

(2) Preparation of Vector for Expressing Antibody Genes

Initially, the serine residue at position 228 was replaced with proline to prevent cleavage of the S—S bond at the hinge region (Angal et al., 1993, Mol. Immunol. 30(1):105-108, Schuurman et al., 2001, Mol. Immunol., 38:1-8), and the DNA of the constant region of IgG4 was divided into four parts, for which sense and antisense DNAs were synthesized and annealed. The annealed fragments were ligated using DNA ligase and inserted into the pcDNA3.1(+) vector (Invitrogen) at the NheI/NotI sites. A multicloning site was also incorporated so that a DNA fragment of the variable region can be inserted.

Next, the gene sequences of the heavy and light chains of the variable region of the humanized PcrV antibody were respectively divided into four, and their sense and antisense DNAs were then synthesized and annealed. The annealed fragments were ligated using DNA ligase and the ligated heavy and light chains were cloned into the MfeI/BlpI and EcoRV/BsiWI regions, respectively. The nucleotide sequences of antibodies were then confirmed.

A mouse-human chimeric 1F3 antibody was prepared as a positive reference of the humanization of antibodies. The sequence of the human IgG4Pro constant region was designed in a heavy chain variable region of a mouse antibody as the constant region sequence of the heavy chain, and an expression plasmid was constructed using the method described below to obtain a plasmid expressing the heavy chain of the mouse/human chimeric antibody (FIG. 13; H chimera). A DNA sequence of conjugated the sequence of the human Igkappa constant region was designed in a light chain variable region of a mouse antibody as the constant region sequence of the light chain, and an expression vector was constructed using the method described above to obtain a plasmid expressing the light chain of the mouse/human chimeric antibody (FIG. 13; L chimera). The heavy and light chain expression plasmids were co-transfected into the mammalian culture cell with any one of the combinations of the plasmids expressing the heavy and light chains of the mouse-human chimeric antibody; the plasmids expressing the heavy and light chains of the template humanized antibody; the plasmids expressing the heavy chain of the template humanized antibody and the light chain of the mutant humanized antibody; the plasmids expressing the heavy chain of the mutant humanized antibody and the light chain of the template humanized antibody; and the plasmids expressing the heavy chain of the mutant humanized antibody and the light chain of the mutant humanized antibody. Each culture supernatants were used to determine the affinity with the antigen recombinant PcrV by surface plasmon resonance analysis (BIAcoreT-100, GE healthcare) (FIG. 13).

The KD value of the mouse-human chimeric antibody obtained by the affinity analysis was $2.6 \times 10^{-10}$ M. The KD value of the antibody including the heavy and light chains of the template humanized antibody was $2.2 \times 10^{-7}$ M; and that of the antibody including the heavy chain of the template humanized antibody and the light chain of the mutant humanized antibody was $6.5 \times 10^{-7}$ M, confirming that the affinity was significantly reduced. In contrast, the KD value of the antibody including the heavy chain of the mutant humanized antibody and the light chain of the template humanized antibody was $3.3 \times 10^{-10}$ M, and that of the antibody including the heavy and light chains of the mutant humanized antibody was $3.4 \times 10^{-10}$ M, indicating that these antibodies retain the affinity closed to that of the mouse-human chimeric antibody. From these results, we concluded that the heavy chain of the mutant humanized antibody is critical for the retention of the affinity and either the light chain of the template humanized antibody or the mutant humanized antibody may be used without altering the affinity. Thus, for the light chain, we selected the light chain of the template humanized antibody, which is more closely related to the human germline-derived sequence. For the heavy chain, a humanized antibody was prepared in which each of the backmutations of the amino acid side chains at H48, H67, H69, H71, H78, H93 and H94 is reverted to those of the human germline-derived sequence respectively, and the affinity with the antigen was assessed by surface plasmon resonance analysis (FIG. 14). As a result, the humanized antibody in which Val at H93 is replaced with Ala showed the KD value of $1.0 \times 10^{-9}$ M, and the humanized antibody in which Leu at H94 is replaced with Arg showed the KD value of $3.2 \times 10^{-7}$ M. Although these antibodies showed reduced affinity, no significant reduction in the affinity was observed in the other humanized antibodies back-mutated to those of the human germline-derived sequence.

These results have verified the sequence of the humanized antibody by using the mouse antibody-derived sequence for H93 and H94 and the human germline amino acid sequence for H48, H67, H69, H71 and H78 (FIGS. 15 and 16). An antibody having this sequence was prepared according to the method described below in (3), and its affinity was confirmed by surface plasmon resonance analysis. As a result, it has been confirmed that this antibody has the same affinity as the mouse antibody (FIG. 17).

(3) Preparation of Recombinant Antibody

The heavy and light chain genes prepared as the method described above were transfected into HEK293F cell using Lipofectamine 2000 (Invitrogen). After 72 hours, the cell supernatant was collected. The recombinant antibody was purified by Protein G affinity column (PIERCE) from the collected cell supernatant.

Example 2

Figure 18:
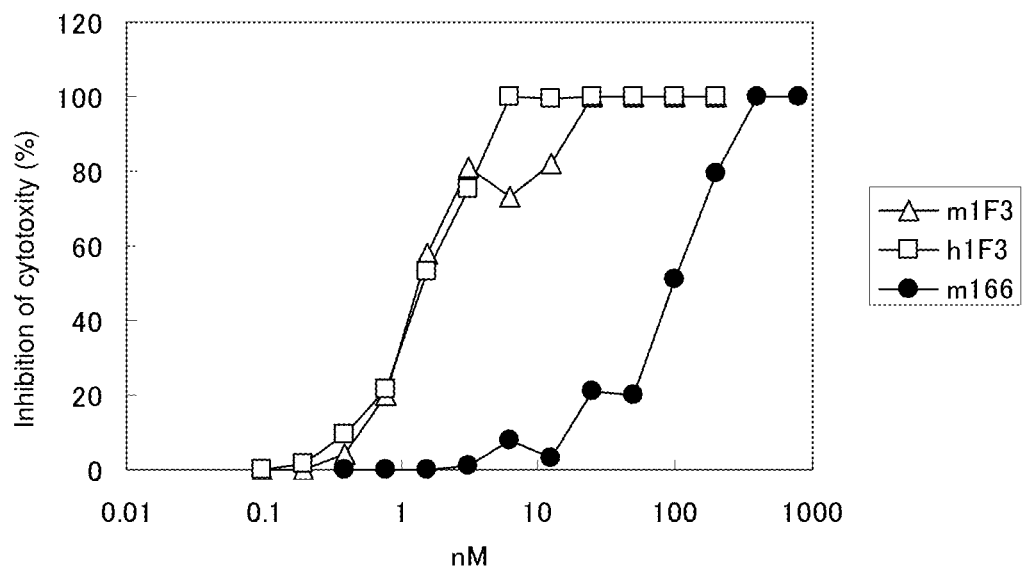
FIG. 18 shows inhibiting effects of PcrV antibodies (humanized PcrV antibody, mouse PcrV antibody and Mab166) on cytotoxicity to U937 cells of *Pseudomonas aeruginosa* strain SR24.
Figure 19:
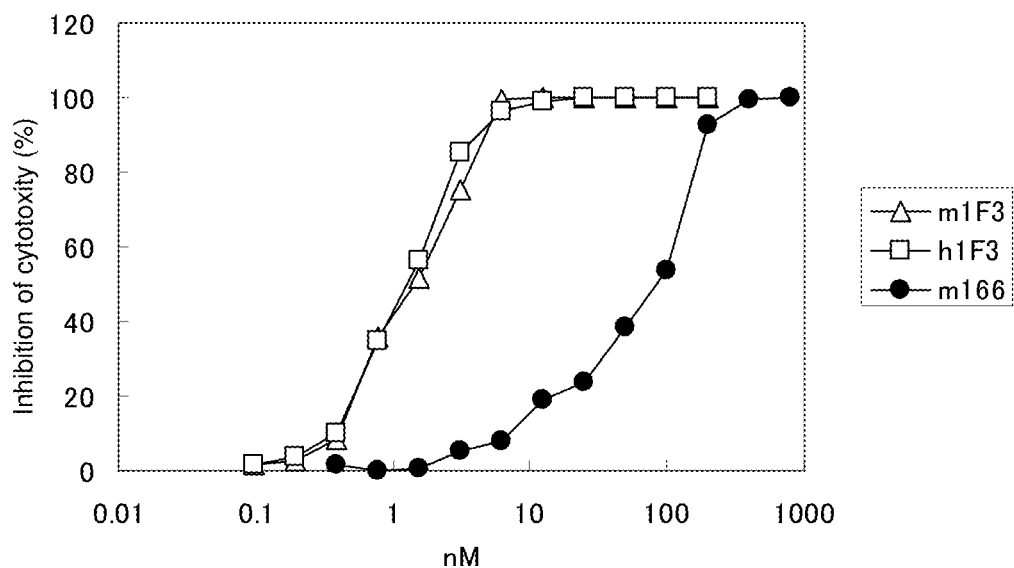
FIG. 19 shows inhibiting effects of PcrV antibodies (humanized PcrV antibody, mouse PcrV antibody and Mab166) on cytotoxicity to myeloma cells of *Pseudomonas aeruginosa* strain SR24.

A cytotoxic inhibitory activity test was performed on m1F3 (mouse antibody), h1F3 (humanized antibody) and m166. The method is as follows:

Initially, m1F3, h1F3 and m166 were diluted by serial doubling dilution starting with 200 nM, 200 nM and 800 nM, respectively. Each dilution (10 µl) was dispensed into the wells of a 96-well microplate. Next, myeloma cell U3P1 or U937 cells were prepared at the cell density of $5 \times 10^6$ or $1 \times 10^6$ cells/ml, respectively, by using a cell culture medium (PRMI1640 (produced by Sigma Corporation), containing sodium hydrogen carbonate and not containing L-glutamine and Phenol Red) and each 70 µl of the suspension was added to the 96-well microplate. Subsequently, the *Pseudomonas aeruginosa* strain SR24 cultured overnight in Cation-adjusted Mueller Hinton Broth (Difco) was prepared at the cell density of $1 \times 10^8$ cfu/ml in the cell culture medium, added to the well in an amount of 10 µl/well, and cultured for 3 hours at 37° C. in a 5% $CO_2$ atmosphere. Three hours later, each 10 µl of WST-8 (produced by Kishida Chemical Co., Ltd.) was added, and the culture was continued for 1 hour at 37° C. in a 5% $CO_2$ atmosphere. After the culture was completed, absorbance was determined at the wavelength of 450 nm. The results showed that the cytotoxic activity (IC50) of m166 was 98.4 nM while m1F3 and h1F3 showed 1.4 nM and 1.5 nM, respectively, when U937 cells were used (FIG. 18), and m166 showed 85.4 nM while m1F3 and h1F3 showed 1.5 nM and 1.3 nM, respectively, when the myeloma cells were used (FIG. 19). Thus, the cytotoxic inhibitory activities of m1F3 and h1F3 were almost the same, and showed higher activity than m166.

INDUSTRIAL APPLICABILITY

The humanized monoclonal antibody of the present invention or a part thereof not only had high affinity with PcrV, but also exhibited strong inhibiting activity on cytotoxicity to eukaryotic cell of *Pseudomonas aeruginosa*. Therefore, the pharmaceutical composition containing the monoclonal antibody or a part thereof is useful as a therapeutic drug for *Pseudomonas aeruginosa*-related infection which is currently considered as being difficult to be treated in medical field.

The invention claimed is:

1. A humanized monoclonal antibody against PcrV having
   1) a heavy chain variable region having amino acid sequence of SEQ ID NO: 27, and
   2) a light chain variable region having amino acid sequence of SEQ ID NO: 28, or antibody fragment thereof.

2. A pharmaceutical composition comprising the antibody or antibody fragment thereof according to claim 1 as an active ingredient and pharmaceutically acceptable carrier.

3. A polynucleotide encoding a heavy chain variable region having the amino acid sequence of SEQ ID NO: 27 or a light chain variable region having the amino acid sequence of SEQ ID NO: 28.

4. An expression vector comprising the polynucleotide according to claim 3.

* * * * *

SEQUENCE LISTING

```
<160> NUMBER OF SEQ ID NOS: 30

<210> SEQ ID NO 1
<211> LENGTH: 294
<212> TYPE: PRT
<213> ORGANISM: Pseudomonas aeruginosa

<400> SEQUENCE: 1

Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
    130                 135                 140
```

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Ser Gly Ser Pro Lys Gln Ser Gly Glu Leu Lys Gly Leu
    210                 215                 220

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
                260                 265                 270

Val Glu Ala Leu Asn Arg Phe Ile Gln Lys Tyr Asp Ser Val Leu Arg
            275                 280                 285

Asp Ile Leu Ser Ala Ile
    290

<210> SEQ ID NO 2
<211> LENGTH: 885
<212> TYPE: DNA
<213> ORGANISM: Pseudomonas aeruginosa

<400> SEQUENCE: 2
atggaagtca gaaaccttaa tgccgctcgc gagctgttcc tggacgagct cctggccgcg      60
tcggcggcgc ctgccagtgc cgagcaggag gaactgctgg ccctgttgcg cagcgagcgg     120
atcgtgctgg cccacgccgg ccagccgctg agcgaggcgc aagtgctcaa ggcgctcgcc     180
tggttgctcg cggccaatcc gtccgcgcct ccggggcagg gcctcgaggt actccgcgaa     240
gtcctgcagg cacgtcggca gcccggtgcg cagtgggatc tgcgcgagtt cctggtgtcg     300
gcctatttca gcctgcacgg cgtctcgac gaggatgtca tcggtgtcta caaggatgtc      360
ctgcagaccc aggacggcaa gcgcaaggcg ctgctcgacg agctcaaggc gctgaccgcg     420
gagttgaagg tctacagcgt gatccagtcg cagatcaacg ccgcgctgtc ggccaagcag     480
ggcatcagga tcgacgctgg cggtatcgat ctggtcgacc ccacgctata tggctatgcc     540
gtcggcgatc ccaggtggaa ggacagcccc gagtatgcgc tgctgagcaa tctggatacc     600
ttcagcggca gctgtcgat caaggatttt ctcagcggct cgccgaagca gagcggggag      660
ctcaagggcc tcagcgatga gtacccttc gagaaggaca caaacccggt cggcaattc      720 gccaccacgg tgagcgaccg ctcgcgtccg ctgaacgaca aggtcaacga agaccacc      780 ctgctcaacg acaccagctc ccgctacaac tcgcggtcg aggcgctcaa ccgcttcatc      840
cagaaatacg acagcgtcct gcgcgacatt ctcagcgcga tctag                     885

<210> SEQ ID NO 3
<211> LENGTH: 33
<212> TYPE: DNA
<213> ORGANISM: Artificial
<220> FEATURE:
<223> OTHER INFORMATION: primer

<400> SEQUENCE: 3
attgcatgca tggaagtcag aaaccttaat gcc                                              33

<210> SEQ ID NO 4
<211> LENGTH: 33
<212> TYPE: DNA
<213> ORGANISM: Artificial
<220> FEATURE:
<223> OTHER INFORMATION: primer

<400> SEQUENCE: 4
tatttcgaag atctagcgcg actcttacag cgc                                              33

<210> SEQ ID NO 5
<211> LENGTH: 27
<212> TYPE: DNA
<213> ORGANISM: Artificial
<220> FEATURE:
<223> OTHER INFORMATION: primer

<400> SEQUENCE: 5
gctcgaggat cccaaggcgc tgaccgc                                                     27

<210> SEQ ID NO 6
<211> LENGTH: 23
<212> TYPE: DNA
<213> ORGANISM: Artificial
<220> FEATURE:
<223> OTHER INFORMATION: primer

<400> SEQUENCE: 6
gttaagcttc tcgaagggta ctc                                                         23

<210> SEQ ID NO 7
<211> LENGTH: 24
<212> TYPE: DNA
<213> ORGANISM: Artificial
<220> FEATURE:
<223> OTHER INFORMATION: primer

<400> SEQUENCE: 7
tagagtcacc gaggagccag ttgt                                                        24

<210> SEQ ID NO 8
<211> LENGTH: 24
<212> TYPE: DNA
<213> ORGANISM: Artificial
<220> FEATURE:
<223> OTHER INFORMATION: primer

<400> SEQUENCE: 8
tccagagttc caagtcacag tcac                                                        24

<210> SEQ ID NO 9
<211> LENGTH: 30
<212> TYPE: DNA
<213> ORGANISM: Artificial
<220> FEATURE:
<223> OTHER INFORMATION: primer

<400> SEQUENCE: 9
aggggccagt ggatagaccg atggggctgt                                                  30

<210> SEQ ID NO 10
<211> LENGTH: 30
<212> TYPE: DNA
<213> ORGANISM: Artificial

```
<220> FEATURE:
<223> OTHER INFORMATION: primer

<400> SEQUENCE: 10
aggggccagt ggatagactg atgggggtgt                                           30

<210> SEQ ID NO 11
<211> LENGTH: 121
<212> TYPE: PRT
<213> ORGANISM: Artificial
<220> FEATURE:
<223> OTHER INFORMATION: VH of Antibody 1F3

<400> SEQUENCE: 11
```

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Asn Thr Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Val Leu Tyr Gly Asn Tyr Val Val Tyr Tyr Thr Met Asp Tyr Trp Gly
            100                 105                 110

Gln Gly Thr Ser Val Thr Val Ser Ser
        115                 120

```
<210> SEQ ID NO 12
<211> LENGTH: 109
<212> TYPE: PRT
<213> ORGANISM: Artificial
<220> FEATURE:
<223> OTHER INFORMATION: VL of Antibody 1F3

<400> SEQUENCE: 12
```

Gln Ile Val Leu Thr Gln Ser Pro Thr Ile Met Ser Ala Ser Leu Gly
1               5                   10                  15

Glu Glu Ile Thr Leu Thr Cys Ser Ala Ser Thr Ser Val Ser Tyr Met
            20                  25                  30

Glu Trp Tyr Gln Gln Lys Ser Gly Thr Ser Pro Lys Ile Leu Ile Tyr
        35                  40                  45

Thr Thr Ser Lys Leu Ala Ser Gly Val Pro Ser Arg Phe Ser Gly Ser
    50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Arg Asn Tyr Pro Phe Thr
                85                  90                  95

Phe Gly Ser Gly Thr Lys Leu Glu Ile Lys Arg Ala Asp
            100                 105

```
<210> SEQ ID NO 13
<211> LENGTH: 120
<212> TYPE: PRT
<213> ORGANISM: Artificial
<220> FEATURE:
<223> OTHER INFORMATION: VH of Antibody 2A4
```

-continued

<400> SEQUENCE: 13

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Asn Gly Asp Thr Ser Tyr Asn Pro Ser Leu
    50                  55                  60

Lys Ser Arg Ile Ser Ile Ala Arg Asp Thr Ser Lys Asn Gln Phe Phe
65                  70                  75                  80

Leu Gln Leu Asn Ser Val Thr Thr Glu Asp Thr Ala Thr Tyr Ser Cys
                85                  90                  95

Ala Gly Ser Arg Asn Tyr Tyr Gly Ala Trp Phe Ala Tyr Trp Gly Gln
            100                 105                 110

Gly Thr Leu Val Thr Val Ser Ala
            115                 120

<210> SEQ ID NO 14
<211> LENGTH: 110
<212> TYPE: PRT
<213> ORGANISM: Artificial
<220> FEATURE:
<223> OTHER INFORMATION: VL of Antibody 2A4

<400> SEQUENCE: 14

Asp Ile Val Met Thr Gln Ser His Lys Phe Met Ser Thr Ser Ile Gly
1               5                   10                  15

Asp Arg Val Ser Ile Asn Tyr Lys Ala Ser Gln Tyr Val Gly Thr Thr
            20                  25                  30

Val Ala Trp Tyr Gln Gln Lys Ser Gly His Ser Pro Lys Leu Leu Ile
        35                  40                  45

Tyr Arg Ala Ser Thr Arg His Thr Gly Val Pro Asp Arg Phe Thr Gly
    50                  55                  60

Ser Gly Ser Gly Thr Asp Phe Thr Leu Asn Ile Ser Asn Val Gln Ser
65                  70                  75                  80

Glu Asp Leu Ala Asp Tyr Phe Cys Gln Gln Tyr Cys Ser Ser Pro Leu
                85                  90                  95

Thr Phe Gly Ala Gly Thr Tyr Leu Glu Val Lys Arg Ala Asp
            100                 105                 110

<210> SEQ ID NO 15
<211> LENGTH: 8
<212> TYPE: PRT
<213> ORGANISM: Artificial
<220> FEATURE:
<223> OTHER INFORMATION: CDR1 of 1F3 heavy chain

<400> SEQUENCE: 15

Ser Phe Thr Ser Tyr Trp Met His
1               5

<210> SEQ ID NO 16
<211> LENGTH: 16
<212> TYPE: PRT
<213> ORGANISM: Artificial
<220> FEATURE:
<223> OTHER INFORMATION: CDR2 of 1F3 heavy chain

```
<400> SEQUENCE: 16

Ile Asn Pro Ser Asn Gly Arg Thr Asn Tyr Asn Glu Lys Phe Asn Thr
1               5                   10                  15

<210> SEQ ID NO 17
<211> LENGTH: 12
<212> TYPE: PRT
<213> ORGANISM: Artificial
<220> FEATURE:
<223> OTHER INFORMATION: CDR3 of 1F3 heavy chain

<400> SEQUENCE: 17

Tyr Gly Asn Tyr Val Tyr Tyr Thr Met Asp Tyr
1               5                   10

<210> SEQ ID NO 18
<211> LENGTH: 10
<212> TYPE: PRT
<213> ORGANISM: Artificial
<220> FEATURE:
<223> OTHER INFORMATION: CDR1 of 1F3 light chain

<400> SEQUENCE: 18

Ser Ala Ser Thr Ser Val Ser Tyr Met Glu
1               5                   10

<210> SEQ ID NO 19
<211> LENGTH: 7
<212> TYPE: PRT
<213> ORGANISM: Artificial
<220> FEATURE:
<223> OTHER INFORMATION: CDR2 of 1F3 light chain

<400> SEQUENCE: 19

Thr Thr Ser Lys Leu Ala Ser
1               5

<210> SEQ ID NO 20
<211> LENGTH: 9
<212> TYPE: PRT
<213> ORGANISM: Artificial
<220> FEATURE:
<223> OTHER INFORMATION: CDR3 of 1F3 light chain

<400> SEQUENCE: 20

His Gln Trp Arg Asn Tyr Pro Phe Thr
1               5

<210> SEQ ID NO 21
<211> LENGTH: 9
<212> TYPE: PRT
<213> ORGANISM: Artificial
<220> FEATURE:
<223> OTHER INFORMATION: CDR1 of 2A4 heavy chain

<400> SEQUENCE: 21

Ser Ile Thr Ser Asp Tyr Ala Trp Asn
1               5

<210> SEQ ID NO 22
<211> LENGTH: 16
<212> TYPE: PRT
<213> ORGANISM: Artificial
<220> FEATURE:
<223> OTHER INFORMATION: CDR2 of 2A4 heavy chain

<400> SEQUENCE: 22
```

Tyr Ile Thr Tyr Asn Gly Asp Thr Ser Tyr Asn Pro Ser Leu Lys Ser
1               5                   10                  15

<210> SEQ ID NO 23
<211> LENGTH: 11
<212> TYPE: PRT
<213> ORGANISM: Artificial
<220> FEATURE:
<223> OTHER INFORMATION: CDR3 of 2A4 heavy chain

<400> SEQUENCE: 23

Ser Arg Asn Tyr Tyr Gly Ala Trp Phe Ala Tyr
1               5                   10

<210> SEQ ID NO 24
<211> LENGTH: 11
<212> TYPE: PRT
<213> ORGANISM: Artificial
<220> FEATURE:
<223> OTHER INFORMATION: CDR1 of 2A4 light chain

<400> SEQUENCE: 24

Lys Ala Ser Gln Tyr Val Gly Thr Thr Val Ala
1               5                   10

<210> SEQ ID NO 25
<211> LENGTH: 7
<212> TYPE: PRT
<213> ORGANISM: Artificial
<220> FEATURE:
<223> OTHER INFORMATION: CDR2 of 2A4 light chain

<400> SEQUENCE: 25

Arg Ala Ser Thr Arg His Thr
1               5

<210> SEQ ID NO 26
<211> LENGTH: 9
<212> TYPE: PRT
<213> ORGANISM: Artificial
<220> FEATURE:
<223> OTHER INFORMATION: CDR3 of 2A4 light chain

<400> SEQUENCE: 26

Gln Gln Tyr Cys Ser Ser Pro Leu Thr
1               5

<210> SEQ ID NO 27
<211> LENGTH: 115
<212> TYPE: PRT
<213> ORGANISM: Artificial
<220> FEATURE:
<223> OTHER INFORMATION: VH of humanized antibody

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
                20                  25                  30

Trp Met His Trp Val Arg Gln Ala Pro Gly Gln Gly Leu Glu Trp Met
            35                  40                  45

Gly Glu Ile Asn Pro Ser Asn Gly Arg Thr Asn Tyr Asn Glu Lys Phe
        50                  55                  60

Asn Thr Arg Val Thr Met Thr Arg Asp Thr Ser Thr Ser Thr Val Tyr 65                  70                  75                  80
Met Glu Leu Ser Ser Leu Arg Ser Glu Asp Thr Ala Val Tyr Tyr Cys
                        85                  90                  95

Val Leu Tyr Gly Asn Tyr Val Val Tyr Thr Met Asp Tyr Trp Gly
            100                 105                 110

Gln Gly Thr
        115

<210> SEQ ID NO 28
<211> LENGTH: 106
<212> TYPE: PRT
<213> ORGANISM: Artificial
<220> FEATURE:
<223> OTHER INFORMATION: VL of humanized antibody

<400> SEQUENCE: 28

Asp Ile Gln Leu Thr Gln Ser Pro Ser Phe Leu Ser Ala Ser Val Gly
1               5                   10                  15

Asp Arg Val Thr Ile Thr Cys Ser Ala Ser Thr Ser Val Ser Tyr Met
            20                  25                  30

Glu Trp Tyr Gln Gln Lys Pro Gly Lys Ala Pro Lys Leu Leu Ile Tyr
        35                  40                  45

Thr Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys His Gln Trp Arg Asn Tyr Pro Phe Thr
                85                  90                  95

Phe Gly Gln Gly Thr Lys Leu Glu Ile Lys
            100                 105

<210> SEQ ID NO 29
<211> LENGTH: 363
<212> TYPE: DNA
<213> ORGANISM: Artificial
<220> FEATURE:
<223> OTHER INFORMATION: DNA encoded VH region

<400> SEQUENCE: 29
caggtgcaat tggtgcagtc tggagccgag gtgaaaaagc caggagcttc cgtaaaagta     60
agctgtaagg cttccgggta tagcttcact tcctactgga tgcactgggt tagacaagca    120
ccaggccagg gcttggagtg gatgggcgag atcaatccat ctaatggcag acaaaactac    180
aacgagaagt tcaatactag agtgaccatg actagagaca caagtacctc caccgtgtat    240
atggagctgt ccagcctgag aagcgaggat actgccgtgt actactgcgt gctgtacggg    300
aactacgtgg tgtattacac aatggactat tgggggcagg gcacaaccgt aaccgtgagc    360
tca                                                                  363

<210> SEQ ID NO 30
<211> LENGTH: 324
<212> TYPE: DNA
<213> ORGANISM: Artificial
<220> FEATURE:
<223> OTHER INFORMATION: DNA encoded VL region

<400> SEQUENCE: 30
gatatccagc tcacacagag tccatccttc ctgagcgcca gcgtcggcga ccgggtaact     60
attacctgct ctgcttcaac cagcgtgtcc tacatggagt ggtatcaaca gaagcccggc    120

```
aaggctccca aactcctgat ctacactaca tccaaactgg ccagcggggt gcccagccgg      180
ttcagcggaa gtgggagtgg aacagagttc acactgacca tttcctccct gcagccagag      240
gatttcgcta cctactattg ccatcagtgg agaaattacc ccttcacctt cggacagggc      300
acaaagctgg agatcaagcg tgct                                            324
```